(12) United States Patent
Wang

(10) Patent No.: US 7,867,766 B2
(45) Date of Patent: Jan. 11, 2011

(54) APPARATUS AND METHOD TO MEASURE THE KINETICS PARAMETERS OF A POROUS POWDER CATALYST

(76) Inventor: Dezheng Wang, Department of Chemical Engineering, Tsinghua University, Beijing (CN) 100084

( * ) Notice: Subject to any disclaimer, the term of this patent is extended or adjusted under 35 U.S.C. 154(b) by 1005 days.

(21) Appl. No.: 11/673,578

(22) Filed: Feb. 11, 2007

(65) Prior Publication Data

US 2007/0196924 A1 Aug. 23, 2007

(30) Foreign Application Priority Data

Feb. 17, 2006 (CN) .................. 2006 1 0011336

(51) Int. Cl.
*G01N 31/10* (2006.01)
*B01J 8/02* (2006.01)
(52) U.S. Cl. .................. 436/37; 422/129; 436/34; 436/50; 436/52; 436/53; 436/134; 436/136; 436/139; 436/140; 436/141; 436/142; 436/155; 436/159; 436/160; 436/173; 436/181
(58) Field of Classification Search .............. 422/129, 422/187–189, 198, 220, 224; 436/34, 37, 436/50, 52–53, 127, 134, 136, 139–142, 436/155, 158–160, 173, 181
See application file for complete search history.

(56) References Cited

U.S. PATENT DOCUMENTS

| | | | | |
|---|---|---|---|---|
| 3,431,077 A | * | 3/1969 | Danforth | 422/80 |
| 3,536,452 A | * | 10/1970 | Norton et al. | 422/63 |
| 4,099,923 A | * | 7/1978 | Milberger | 422/80 |
| 4,221,568 A | * | 9/1980 | Boettger | 436/48 |
| 5,009,849 A | * | 4/1991 | Ebner et al. | 422/83 |
| 5,264,183 A | | 11/1993 | Ebner et al. | |
| 5,376,335 A | | 12/1994 | Gleaves | |
| 5,523,063 A | * | 6/1996 | Anderson | 422/224 |

(Continued)

OTHER PUBLICATIONS

Wang, D. et al, Journal of Catalysis 1996, 159, 418-426.*

(Continued)

*Primary Examiner*—Arlen Soderquist
(74) *Attorney, Agent, or Firm*—Robert A. deGroot

(57) ABSTRACT

An apparatus and method are disclosed for measuring the kinetic parameters of a catalyst powder, which include the reaction rate constants, active site concentration and intraparticle diffusivity. The measurement of the active site concentration selectively measures just the active sites and not the entire exposed atom concentration. The apparatus and method use surface concentrations less than 50% and larger than 1% the total active site concentration and a dynamic pulsed flow to avoid including weak adsorption sites not involved in the catalysis. The measurement is more accurate because (1) it uses a reactant gas and non-steady state adsorption at temperatures near to reaction temperatures, and (2) it uses the chemical kinetics expressions to extract the measured active site concentration to perform the measurement so as to count just those sites actually active for that reactant. This is better than the prior art methods that measure an entire surface atom concentration under non-dynamic conditions because the latter is not necessarily the same as the active site concentration in the chemical kinetics expression. The intraparticle diffusivity measured by the apparatus and method is the effective gas diffusivity in a porous powder, and this is useful as a characterization of the tortuosity of the porous powder.

7 Claims, 6 Drawing Sheets

U.S. PATENT DOCUMENTS 6,227,694 B1 * 5/2001 Mitake et al. ............ 366/162.4
7,435,598 B2 * 10/2008 Vaughn et al. ................ 436/37

OTHER PUBLICATIONS

Shuurman Y. et al, Catalysis Today 1997, 33, 25-37.*
Gleaves, J. T. et al, Applied Catalysis A: General 1997, 160, 55-88.*
Randall, H. T. et al, Studies in Surface Science and Catalysis 1999, 122, 209-218.*
Dewaele, O. et al, Journal of Molecular Catalysis A: Chemical 1999, 149, 263-273.*
Perez-Ramirez, J. et al, Catalysis Today 2000, 60, 93-109.*
Olea, M. et al, Bulletin of the Chemical Society of Japan 2001, 74, 255-265.*
Wang, D. et al, Studies in Surface Science and Catalysis 2001, 133, 553-557.*
Ma, D. et al, Journal of Catalysis 2002, 208, 260-269.*
Wang, D. et al, Chemical Engineering Science 2003, 58, 887-893.*
Wang, D. et al, Chemical Engineering Science 2004, 59, 5615-5622.*
Gao, L. et al, Studies in Surface Science and Catalysis 2006, 159, 677-680.*
Li, W. et al, Catalysis Today 2007, 121, 246-254.*
Shuurman, Y. et al, Catalysis Today 1997, 38, 129-135.*
Tang, S. et al, Catalysis Letters 1998, 55, 83-86.*
Shekhtman, S. O. et al, Chemical Engineering Science 1999, 54, 4371-4378.*
Yablonsky, G. S. et al, Journal of Catalysis 2003, 216, 120-134.*

* cited by examiner

APPARATUS AND METHOD TO MEASURE THE KINETICS PARAMETERS OF A POROUS POWDER CATALYST

CROSS-REFERENCE TO RELATED APPLICATIONS

Priority is claimed pursuant to 35USC119a,b from People's Republic of China patent application number 200610011336.3, filed on Feb. 17, 2006.

TECHNICAL FIELD AND INDUSTRIAL APPLICABILITY OF THE INVENTION

This invention relates to the characterization of powder catalysts used in heterogeneously catalyzed chemical processes. Powder catalysts are presently made by methods that give highly variable efficiencies. The present invention relates particularly to a more accurate characterization of their kinetic parameters, such as the reaction rate constants, active site concentration, and gas diffusivity in the powder, and is useful for evaluating the efficiency of a preparation method.

BACKGROUND OF THE INVENTION

In this invention, the term "kinetics parameters" includes the reaction rate constants, active site concentration, and gas diffusivity. The terms "reaction rate constant" and "gas diffusivity" are used conventionally as defined and discussed in chemical kinetics texts. Here, the term "active site" is used in a narrower sense than is usual in describing powder catalysts as follows. "Active site" refers to an atom or a group of atoms on a solid catalyst where a reactant gas adsorbs fast enough to maintain a catalytic reaction cycle, an active site is defined experimentally by the reactant gas, and the active sites for different reactants may be different. "Active" means catalytic. The active site concentration is the amount of active sites per weight of catalyst powder.

The term "active site concentration" used here is different from the term "specific surface area" often used to describe catalyst powders. The latter means the entire surface. It is now understood that when a solid surface is used as a catalyst, for many reactions it is only a fraction of the surface that is active, not its entire exposed surface. However, there has been no means that can selectively measure just the active fraction. The methods used to normalize for the amount of catalyst or catalytic sites have to make do with the use of the entire surface. But, because the active fraction need not be the same for all catalyst surfaces, normalization by the entire surface can be misleading. The present invention meets the need for a means to selectively measure just the active fraction of the surface.

Powders in common use as catalysts in heterogeneously catalyzed processes are made by methods that give highly variable active site concentrations. The measurement of the active site concentration is useful for evaluating the efficiency of a preparation method. It is also useful for comparing the catalytic activity of different catalysts because the comparison is made on a more fundamental basis when the reaction rate is normalized by dividing by the active site concentration to give a comparison that uses the rate per active site.

As mentioned, the presently used method to normalize a reaction rate with respect to the used amount of catalyst actually uses the entire surface area of a powder. In the prior art methods, this entire surface area is determined by measuring the amount of gas adsorbed when the surface had been adsorptively saturated. The gas amount adsorbed, known as the monolayer amount, is converted into a surface area using the cross-sectional area of the adsorbed molecule. A commonly used method uses the pulsing of a series of similarly sized gas pulses, also known to those skilled in the art as the pulse or flow chemisorption method. This uses the decrease in the peak area, due to adsorption, of the chromatogram of the series of pulsed gas to determine the amount of adsorbed gas. This method has the defect that the measurement is carried out until repeated pulsing of the same sized pulse shows that consecutive pulses have the same peak area. This is a fundamental defect because the repeated pulsing provides for adsorption to saturation of the entire surface or multiple adsorption on the same site.

The present invention uses a different principle to determine the active site concentration when gases are pulsed that avoids these defects.

Other specific methods to determine the specific surface area include the method known as the BET measurement, which includes the static volumetric method, flow method, and gravimetric method, and the static volumetric method of chemisorption measurement, which are described in standard texts on the characterization of catalysts. It is a defect in all these methods that they perform their measurements until there is no further change in the gas phase concentration or pressure, which is their criterion that determines when adsorption saturation is reached. All these prior art methods may be inaccurate because this means to verify saturation requires the catalyst surface to be equilibrated with the gas phase for at least a few minutes and in many cases, some tens of minutes. The equilibration contact with a gas phase for a period of time has the defect that it causes the loss of an important distinction between sites, namely, the ability to distinguish sites of different adsorption energies or rates. The long equilibration times leads to the occupation of all the adsorption sites, including sites where adsorption is too weak or slow for a reasonable reaction rate; thus, it causes the loss of the distinction of sites with different adsorption energies or rates.

Another shortcoming of the prior art methods that measure the surface area is that they must use non-reactive conditions. This is because these methods use long equilibration times or a long series of pulses. This precludes the use of reactive conditions since these equilibration times or pulse series are long enough that were a reaction to occur, it will consume adsorbed gases to give multiple adsorption and situations where the amounts dosed are different from the amounts existent on the surface. E.g., in the prior art methods, a non-reactive room temperature must be used when gases like hydrogen or carbon monoxide are used with metal surfaces. This constraint of the measurement conditions to non-reactive conditions has the defect that the measured quantity does not have a direct relationship with the (concentration of) active sites where reactants under reaction conditions react, thus, the measurement may be inaccurate.

In chemical kinetics, the adsorption rate is calculated by the chemical kinetics expression:

$$r_{ads} = k'_{ads} C_A (C_0 - C_{A,ads}),$$

where $r_{ads}$ is the adsorption rate, $k'_{ads}$ is the adsorption rate constant per active site, $C_A$ is the concentration (or pressure) of the adsorbing gas, $C_0$ is the active site concentration, and $C_{A,ads}$ is the surface species concentration. The per site adsorption rate constant, $k'_{ads}$, used in the equation above differs by a multiplication factor equal to the active site concentration from the adsorption rate constant per unit weight powder (or per unit volume reactor, depending on the units used for the active site concentration) that is more commonly used in chemical kinetics texts. It is another defect of prior art methods that the active site concentration in this expression is not directly measured. Instead, the prior art methods first measure an entire surface area independently of the chemical kinetics expression, and then assume that this measured quantity is the same as the active site concentration in the kinetic expression when it is used in calculating the adsorption rate. Since it need not be the case that this entire surface area is the same as the active site concentration, $C_0$, in the kinetics expression, the result may be inaccurate.

U.S. Pat. No. 5,264,183 issued to Ebner and Gleaves and U.S. Pat. No. 5,376,335 issued to Gleaves described pulsed valve apparatuses that are used to study the elution sequence of the reaction intermediates in a catalyzed reaction using the response curves of product gases. These apparatuses, reportedly used for the analysis of the sequence in which the reaction steps occur, have the defect that they cannot measure the active site concentration of the catalysts by the principle developed in this invention because they have no provisions for individual gas pulses to make detectable changes to the surface concentration. Contrariwise, the objects of the '183 and '335 patents require conditions where the amount of active sites of the catalyst powder sample is far more than the molecules in a gas pulse used, which makes it not possible to obtain the active site concentration of the catalysts because each gas pulse can then only make a negligible change to the surface concentration on the catalyst. Furthermore, the use of a pulsed gas technique requires the gas to be delivered rapidly, but the apparatuses described in the '183 and '335 patents include a mixing chamber or narrow channels or "zero-volume manifold" between the valve and reactor, which leads to undesirable pulse broadening.

A recent variant of the pulse or flow chemisorption method that used the apparatus described in the '335 patent used a series of similarly sized gas pulses that were injected until a change in the transient response (response curve) of a gas (either that injected or a product gas) showed that a change in the state of a catalyst had been effected by the many pulses. The amount of gas in this long series of same size gas pulses, and the modeling of the change in the shape or moments of the response curve caused by these, with the procedure experimentally controlled so that it needed very many pulses to cause a change in the response curve, was said useable to determine the amount of active sites. This method also has the defect that it uses the repeated pulsing of many intermittent pulses, which provides for adsorption on the entire surface or multiple adsorption on the same site.

In this invention, the term "gas diffusivity" refers to the effective diffusivity that is used when a gas-solid two phase system is viewed as a pseudo-homogeneous one phase medium. This is generally expressed as the diffusivity times porosity divided by tortuosity. "Intraparticle diffusivity" refers to the gas diffusivity inside a porous solid. The speed with which a gas can reach and exit the inside of a porous solid is an important kinetic parameter in many uses of porous powders. The intraparticle diffusivity is the measure of this property. Readily available techniques for measuring the intraparticle diffusivity in porous materials include the methods of permeability, Wilke-Kallenbach, time lag, sorption rate measurement, efficiency factor, frequency response, chromatographic methods, pulsed-field gradient NMR, and quasielastic neutron scattering, which are described in standard texts on diffusion in porous solids. However, none of these techniques have received widespread use because they either need large crystalline samples or expensive instruments or require very extensive measurements or are not precise. There is a need for an apparatus and a method that is simple, convenient to use, and precise enough, which is provided by this invention.

Previously, a pulsed valve apparatus of the type described in the '183 patent had been used for measuring the configuration diffusivity of strongly interacting gases in a zeolitic microporous powder packed bed by measuring the transient response (response curve) that elutes from the packed bed and using reactor simulation and regression to estimate the diffusivity. However, this was designed for use with the type of microporous powder and gas in which the gas interacts with the walls of the pores inside the powder. Generally, this interaction is one that causes the gas to stick onto the wall and because of this sticking interaction, it can only move slowly inside the pores or along the wall while stuck to the wall. This interaction has the effect that the elution of the gas from the packed bed is quite slow. Then, to avoid the appearance of response curves that are too much broadened, packed beds that are very short, generally less than 5 mm, are used. This has the disadvantage that with powders and gases where the gas does not interact with the walls except for collisions, in which there is no pulse broadening due to an interaction between the gas and wall, there is only limited precision in the measurement of the intraparticle diffusivity. There is a need for an apparatus and a method that can give improved precision, which is provided by this invention.

The measurement technique used in this invention is part of the art generally referred to as "relaxation kinetics". Relaxation kinetics is implemented by a device that makes a sharp change, e.g. as a pulse or step injection, in the concentration of a molecular species delivered to a sample. Phenomena amendable to study can be limited by degradation of the sharpness of the pulse or step edge delivered to the sample because the information on these phenomena are extracted from the further change to the pulse or step edge shape, but if the "sharp" pulse or step edge is not sharp but occurs over a time extent longer than the characteristic time of the phenomenon, the further change due to the phenomenon will be small and cannot be reliably determined from the experimental data.

Prior art devices to transmit gas inputs from orifice openings to a sample under vacuum have the defect that they include at least a narrow channel and may further include a mixing chamber or some other protrusions between the point of injection and the sample. These include the devices described in the above '183 and '335 patents. When the gas delivery is performed under very low pressure conditions, these devices are flawed because at low pressures, broadening of a pulse or step edge is determined by the frequency of gas collisions with the channel wall or any added surfaces. Thus, the use of a narrow channel or mixing chamber or added solid surface is a fundamental defect because these increase the frequency of gas-solid collisions and cause pulse or edge broadening. This invention is also directed towards a device to deliver gas inputs from orifice openings to a sample under vacuum that has an increased rate of transmission and thus less degradation of the sharpness with which attached injection devices can make such sharp changes in concentration.

This invention is also an improvement over prior devices in simplifying the mathematical modeling for the quantitative extraction of information by parameter fitting. The kinetics parameters in the kinetics expressions can be extracted when a complete mathematical description of the flow of the molecular species or gases can be made. Here, the space where the flow of the gas occurs, which includes the space between a mechanical device that makes a concentration change and a device that removes the gas, and includes the catalyst powder and a detector means, is called the flow path. A complete mathematical description can be made when the geometry of the flow path is well defined and maintained under Knudsen flow conditions. This invention is further directed towards increasing the accuracy and tractability of a mathematical representation of the flow path by the use of a cylindrical geometry and means for a rapid expansion of gas input to a low pressure and Knudsen flow conditions.

BRIEF SUMMARY OF THE INVENTION

In accordance with a first aspect of this invention, there is provided a device for the low pressure delivery of feed gas for measuring kinetics parameters comprising:
(a) a sample tube which is cylindrical and demountable;
(b) a metal block having a smoothed-wall, cylindrical cavity in immediate communication with one end of the sample tube, wherein the cavity has a diameter at least as large as the diameter of the sample tube and the cavity has at least one valved opening on its circumference;
(c) valving means for opening the valved opening for injection of feed gas, and;
(d) a vacuum chamber and a vacuum pump in communication with the other end of the sample tube.

The device for the low pressure delivery of feed gas for measuring kinetics parameters wherein any point within the cavity has a line of sight with all of the sample tube.

The device for the low pressure delivery of feed gas for measuring kinetics parameters wherein the volume of the cavity is at least 0.1 ml.

In accordance with a second aspect of this invention, there is provided an apparatus for measuring the kinetics parameters of a catalyst powder comprising:
(a) a cylindrical, demountable sample tube having a packed bed comprising at least the catalyst powder;
(b) a metal block having a smoothed-wall, cylindrical cavity in immediate communication with the upstream end of the sample tube, wherein the cavity has a diameter at least as large as the diameter of the sample tube and the cavity has a plurality of valved openings on its circumference;
(c) means for injecting cleaning gas through a first valved opening;
(d) means for pulse injecting of feed gas through a second valved opening, wherein the pulsed gas amount is sufficiently small to satisfy the condition for Knudsen flow;
(e) a furnace that encloses the packed bed;
(f) gas removing means in communication with the downstream end of the sample tube;
(g) at least one gas concentration measuring means in communication with the downstream end of the sample tube; and
(h) a data acquisition and treatment system in communication with the gas concentration measuring means.

The apparatus for measuring the kinetics parameters of a catalyst powder wherein the gas removing means is a cylindrical vacuum chamber with a vacuum pump with pumping speed at least 1500 liters per second attached at the outlet end, and wherein the gas concentration measuring means is attached inside the vacuum chamber and the vacuum chamber is empty except for the gas concentration measuring means.

The apparatus for measuring the kinetics parameters of a catalyst powder wherein the gas removing means is alternatively an exhaust, a roughing pump, or a cylindrical vacuum chamber and a vacuum pump with pumping speed at least 1500 liters per second attached at the outlet end, and wherein the gas concentration measuring means is attached inside the vacuum chamber and the vacuum chamber is empty except for the gas concentration measuring means.

The apparatus for measuring the kinetics parameters of a catalyst powder wherein the cavity in the metal block has a volume that is at least 0.1 ml.

The apparatus for measuring the kinetics parameters of a catalyst powder wherein the packed bed is at least 7 mm long but sufficiently short so that the bed diffusion time constant is less than the intraparticle diffusion time constant in the catalyst powder.

The apparatus for measuring the kinetics parameters of a catalyst powder wherein the means for pulse injecting is an electronically controlled solenoid valve that injects gas pulses of varied size comprising at least one reactant and an inert gas, wherein the largest and smallest pulses differ by at least ten-fold, and wherein the amount of active sites on the catalyst powder is less than $2.5 \times 10^{17}$ sites.

In accordance with a third aspect of this invention, there is provided an apparatus for measuring the active site concentration of a catalyst powder comprising:
(a) a metal block having a cavity with a plurality of valved openings on the cavity circumference;
(b) means for injecting cleaning gas through a first valved opening;
(c) means for pulsed injecting of feed gas through a second valved opening, wherein the pulsed gas amount is sufficiently small to satisfy the condition for Knudsen flow;
(d) a demountable sample tube having at least the catalyst powder disposed as a packed bed which is attached at the upstream end to the mouth of the cavity, wherein the number of active sites on the catalyst powder is less than 100 times the number of adsorbate fragments in the largest gas pulse that is sufficiently small to satisfy the condition for Knudsen flow;
(e) a furnace that encloses the packed bed;
(f) gas removing means in communication with the downstream end of the sample tube;
(g) at least two gas concentration measuring means in communication with the downstream end of the sample tube; and
(h) a data acquisition and treatment system in communication with the gas concentration measuring means.

The apparatus for measuring the active site concentration of a catalyst powder wherein the gas removing means is a cylindrical vacuum chamber with a vacuum pump with pumping speed at least 1500 liters per second attached at the outlet end, and wherein the gas concentration measuring means are attached inside the vacuum chamber and the vacuum chamber is empty except for the gas concentration measuring means.

The apparatus for measuring the active site concentration of a catalyst powder wherein the gas removing means is alternatively an exhaust, a roughing pump, or a cylindrical vacuum chamber with a vacuum pump with pumping speed at least 1500 liters per second attached at the outlet end, and wherein the gas concentration measuring means are attached inside the vacuum chamber and the vacuum chamber is empty except for the gas concentration measuring means.

The apparatus for measuring the active site concentration of a catalyst powder wherein the means for pulsed injecting is an electronically controlled solenoid valve that injects gas pulses of varied size comprising at least one reactant and an inert gas, wherein the largest and smallest pulses differ by at least ten-fold.

The apparatus for measuring the active site concentration of a catalyst powder further including an auxiliary packed bed of inert particles comprising a particle size between 1 and 200 micron disposed downstream of the packed bed.

The apparatus for measuring the active site concentration of a catalyst powder wherein the packed bed is of sufficient length so that the bed diffusion time constant is larger than the intraparticle diffusion time constant in the catalyst powder, and wherein the packed bed may include a diffusively similar inert powder to get it to the required length.

The apparatus for measuring the active site concentration of a catalyst powder wherein the cavity in the metal block is smooth-walled, cylindrical, and in immediate communication with the sample tube.

In accordance with a fourth aspect of this invention, there is provided a method for measuring the active site concentration of a catalyst powder, comprising the steps:
(a) providing a metal block having a cavity with a plurality of valved openings on the cavity circumference;
(b) providing valving means for a first valved opening and preparing a cleaning gas therein;
(c) providing pulsed valving means for a second valved opening and preparing a feed gas comprising at least one reactant and an inert gas therein;
(d) providing a demountable sample tube, disposing at least the catalyst powder as a packed bed therein, and attaching it at the upstream end to the mouth of the cavity, wherein the number of active sites on the catalyst powder is less than 100 times the number of adsorbate fragments in the largest gas pulse that is sufficiently small to satisfy the condition for Knudsen flow;
(e) providing gas removing means that is in communication with the downstream end of the sample tube;
(f) providing a furnace that encloses the packed bed;
(g) heating and cleaning the catalyst powder by a delivery of cleaning gas using the valving means and removing gas using the gas removing means;
(h) stopping the delivery of cleaning gas and desorbing adsorbed gas from the catalyst powder by heating and removing gas using the gas removal means to provide a vacuum in the sample tube;
(i) providing for the packed bed to be at an adsorption temperature, using the pulsed valving means to deliver a feed gas pulse into the sample tube, and removing gas using the gas removal means, wherein the feed gas pulse is sufficiently small so that the feed gas flows in Knudsen flow;
(j) providing at least two gas concentration measuring means that are in communication with the downstream end of the sample tube, measuring the response curves of the inert gas and at least one reactant as they are removed, and using the area of the inert gas response curve to calculate the injected pulse size; and
(k) using a mathematical model and fitting at least the response curve of the reactant to extract the active site concentration on the catalyst powder.

The method for measuring the active site concentration of a catalyst powder further including repeating steps (g) to (k) using a different pulse size in step (i), wherein the largest and smallest pulses differ by at least ten-fold.

The method for measuring the active site concentration of a catalyst powder wherein the gas removing means in step (e) is a cylindrical vacuum chamber with a vacuum pump with pumping speed at least 1500 liters per second attached at the outlet end, and wherein the gas concentration measuring means are attached inside the vacuum chamber and the vacuum chamber is empty except for the gas concentration measuring means.

The method for measuring the active site concentration of a catalyst powder wherein the gas removing means in step (e) is alternatively an exhaust in step (g), a roughing pump in step (h), or a cylindrical vacuum chamber with a vacuum pump with pumping speed at least 1500 liters per second attached at the outlet end in step (i), and wherein the gas concentration measuring means are attached inside the vacuum chamber and the vacuum chamber is empty except for the gas concentration measuring means.

The method for measuring the active site concentration of a catalyst powder wherein the cavity in step (a) is at least 0.1 ml in volume and in immediate communication with the sample tube.

The method for measuring the active site concentration of a catalyst powder further including disposing an auxiliary packed bed of inert particles comprising a particle size between 1 and 200 micron downstream of the packed bed in step (d).

The method for measuring the active site concentration of a catalyst powder wherein the packed bed in step (d) is of sufficient length so that the bed diffusion time constant is larger than the intraparticle diffusion time constant in the catalyst powder, and wherein the packed bed may include a diffusively similar inert powder to get it to the required length.

The method for measuring the active site concentration of a catalyst powder further including measuring the response curves of at least one product gas in step (j) and fitting the response curve of the product gas in step (k).

The objects and advantages of the invention are to provide an apparatus for measuring the kinetics parameters of a catalyst powder, including the rate constants, active site concentration and gas diffusivity, an apparatus and method for measuring the active site concentration on a catalyst powder, and a device for the low pressure delivery of feed gas in such apparatuses, wherein one aspect is the measurement of the active site concentration on a catalyst powder that does not use a means that requires the measurement to be carried out until the entire surface of the catalyst powder gets adsorptively saturated, that is, its measured active site concentration avoids the inclusion of surface sites where adsorption is weak or slow and that do not play any role in catalysis. This invention provides a much more accurate measurement since it uses transient adsorption and a surface species concentration less than the active site concentration. Another aspect is the use of reactant molecules and near reaction temperatures to provide the adsorbed species. By this means, its measurement includes only the active sites pertinent to these molecules where the catalysis is actually occurring. Another aspect is the use of the adsorption rate chemical kinetics expression to extract the measured active site concentration, which makes the measurement more accurate since this ensures a direct relationship with the chemical kinetics. Another aspect is the measurement of gas diffusivity that use ordinary powders made as a long packed bed where it is the length of the bed that is at least 7 mm that provides a higher precision. This is highly significant since this does not need large crystalline samples.

This invention has the effect and advantages that the measurement of the active site concentration of a catalyst powder is more accurate because, as distinct from prior art, it selectively measures just the active site concentration of the exposed surface and not the entire exposed atom concentration, where the latter includes inactive surface.

The advantages of the invention are:
(1) The use of surface species concentrations significantly less than the active site concentration and transient adsorption. This is highly significant because it avoids the inclusion of surface sites where adsorption is weak or slow and do not play any role in catalysis and it differs from the prior art methods that measure the entire surface atomic concentration.

(2) The invention's experimental results are of higher accuracy because it uses a reactant gas and temperatures near reaction temperatures to measure only the active sites pertinent to that gas where the catalysis is actually occurring and it differs from the prior art methods that use an inert gas and non-reactive temperatures.

(3) The invention's experimental results are of higher accuracy because it uses the adsorption rate expression to extract the measured active site concentration. This differs from and is a big improvement over the prior art methods that measure under non-kinetic conditions an entire surface area, which is not necessarily the same as the active site concentration term in the adsorption rate expression.

(4) As distinct from the apparatuses and processes of the '183 and '335 patents, this invention differs in providing: (1) the catalyst amount to be chosen to provide for a gas pulse to cause more than 1% of the active sites to be occupied, (2) the injection of a gas pulse through a cavity that minimizes surface collisions and provides much faster gas transmission, (3) the injection of a range of gas pulse sizes, where in this range detectable changes in the normalized pulse shape of the eluted reactant gas occur, and (4) the simultaneous measurement of the pulse shapes of a reactant gas and an inert internal standard gas to give a more accurate measure of the pulse size.

Figure 1:
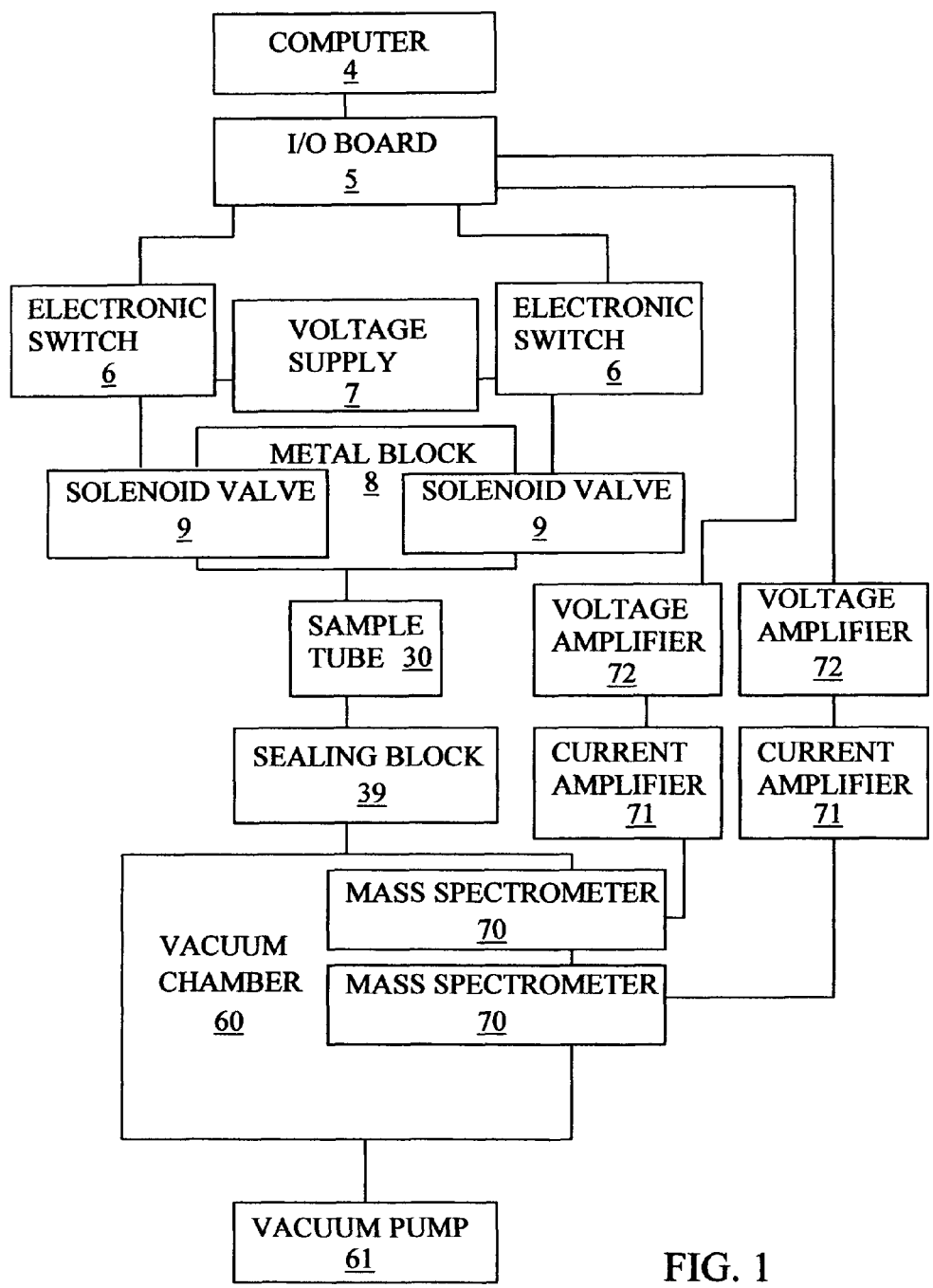
FIG. 1 is a schematic view of an apparatus (embodiment 1) to measure the active site concentration of a catalyst powder.

4—computer; 5—I/O board; 6—electronic switch; 7—voltage supply; 8—metal block;
8A—metal block; 9—solenoid valve; 10—cavity; 10A—cavity;
11—orifice; 12—valve stem; 13—stem channel;
14—rubber tip; 15—spring; 16—solenoid; 17—soft iron piece; 18—tubing;
19—sealing means-A; 20—threaded flange; 21—gas supply; 22—O-ring rubber gasket-A;
23—stainless steel ring-A; 24—threadpiece-A; 25—threaded means-A; 27—metal plate;
28—sealing means-C; 30—sample tube; 31—packed bed; 32—furnace;
33—auxiliary packed bed; 39—sealing block; 40—sealing block-A;
41—three-way ball valve; 42—O-ring rubber gasket-B; 43—stainless steel ring-B;
44—threadpiece-B; 45—threaded means-B; 46—conduit-A; 47—conduit-B; 48—conduit-C;
49—conduit-D; 50—rotary plug; 51—handle; 60—vacuum chamber; 61—vacuum pump;
62—exhaust; 63—roughing pump; 68—sealing means-B; 69—mounting rod;
70—mass spectrometer; 71—current amplifier; 72—voltage amplifier;

DETAILED DESCRIPTION OF THE INVENTION—PREFERRED EMBODIMENT 1

This invention measures the active site concentration of a powder catalyst by pulsing individual gas pulses to flow through a powder catalyst by Knudsen flow. It is novel in providing for that as a pulse flows by in Knudsen flow, it adsorbs on the powder catalyst to give an adsorbed surface concentration that is a measurable fraction of but substantially less than the active site concentration. "Measurable fraction" here means a fraction large enough to decrease the adsorption rate so that the response curve is measurably changed from that of the clean surface, and is roughly a fraction more than 1%. "Substantially less" is roughly a fraction less than 50%, and should be also understood as operationally defined as not too large so that it produces a response curve that is measurably changed from that of the fully occupied surface. The use of a surface concentration that is substantially less than the active site concentration avoids the use of long adsorption times. The invention uses the injection of individual fast and small gas pulses into a packed bed containing the catalyst powder kept under vacuum. The principle of the measurement will be first described, then the apparatus, and finally the procedure for making a measurement.

In principle, one pulse can be sufficient for the measurement, but it is preferred, for good parametric sensitivity and statistical confidence, to use a number of pulses of different sizes and locate the size range where the biggest changes in the normalized reactant response occur as the pulse size changes to find the pulse sizes that give good parametric sensitivity. The largest and smallest pulses should differ by at least ten-fold. The response curves of the different sizes should be all used, with appropriate weighting, in the parameter fitting, but, although a number of pulses are used, this is to provide better statistical confidence, with each pulse being fitted to the same kinetic parameters. Each pulse must be small enough to give only a very low pressure in the bed so that the gas pulse flows through the bed by Knudsen diffusion (molecular flow). The response curves of the gases are measured. The normalized response curves from the different pulse sizes are compared to find the range of pulse sizes where the reactant (or product) curves change shape while the inert gas curves do not change shape. The reactant curves as a function of the pulse size are the data used by a parameter fitting routine to extract the active site concentration. Herein, a "response curve" means a curve of the concentration measured versus time in a vacuum chamber due to the gas eluted from a pulse injection and "normalized" means the curve obtained by dividing the concentration by the maximum concentration of the curve, and expressed as percentage (or fraction) of the maximum concentration. It is easier to see shape changes with normalized curves, while it is better to use non-normalized curves for parameter fitting. The changes in the reactant response curves are due to changed adsorption rates caused by the changed occupied fractions of the active site concentration from the different pulse sizes.

The basis of the measurement is that the mass transport equation (continuity equation) and its solution for a gas pulse flowing in Knudsen flow through a powder bed is not pulse size (pressure) dependent when the surface species concentration due to gas adsorption is small, and is pulse size (pressure) dependent when the surface species concentrations are substantial (about >1% of active site concentration).

In the Knudsen flow regime, the gas species mass transport equation is:

$$\varepsilon_b(x)\frac{\partial C_A}{\partial t} = \frac{1}{A(x)}\frac{\partial}{\partial x}A(x)D_{e,A}(x)\frac{\partial C_A}{\partial x} \pm ads/desb \text{ terms} \quad (1)$$

The mathematical description that the gas is injected as a gas pulse is given in the initial and boundary conditions, with the initial condition:

$0 \leq x \leq L$, $t=0$, $C_A=0$ and the boundary conditions at the entrance of the reactor and exit of the vacuum chamber:

$x = 0$ = pulse injection, (Rectangle function pulse)

$t \geq 0$, $$-D_{e,A}(0)A(0)\frac{\partial C_A}{\partial x}\bigg|_0 = R(\tau)N_{pA}$$

$x = L$ = pump entrance, $t \geq 0$, $$-D_{e,A}(L)A(L)\frac{\partial C_A}{\partial x}\bigg|_L = S_p C_A(L)$$

$C_A(x)$ is the partial pressure of gas A at position x. $D_{e,A}(x)$ is the effective diffusivity of the gas A at position x (it is an adjustable parameter at the positions of the packed bed and is 130 $d_r m^2/s$ where there is void space of diameter $d_r$). L is the length of the diffusion path from the point of pulse delivery through the powder bed to the vacuum pump entrance (when pumps with less than about 3000 $ls^{-1}$ pumping speed are used, it may be necessary to take the length to the vacuum pump entrance, as above; else it may be assumed that the pumping speed is infinitely fast and the gas concentrations in the vacuum chamber are zero). $\varepsilon_b(x)$ is the porosity (it is 1.0 where there is void space). $R(\tau) N_{pA}$ represents the gas delivery as a rectangle pulse function of duration time $\tau$ (in the apparatus here, $\tau$ is 0.8 ms) with pulse amount per time $N_{pA}$. $A(x)$ is the cross-section area at position x. $S_p$ is the pumping speed of the vacuum pump.

In the parameter fitting, it is better to first use data from empty tubes to establish the parameters of the vacuum chamber present in the mathematical description. Particular models used to describe the gas flow can have different parameters. For example, a model may use as the parameters of the vacuum chamber the diffusivity of void space and the pumping speed at the vacuum pump entrance, and use data from two empty tubes of different length to fit for these. Another model may further include a description of the gas flow in the quadruple mass filters, and add as parameters the fraction of gas that diffuses into and the diffusivity inside the quadruple mass filters and use data from four empty tubes of different length. The model used depends on the precision desired. The procedure is well known to those skilled in the art.

The ads/desb terms in equation 1 comprise the chemical kinetics equations for the adsorption and desorption rate, which can be written:

$r_{ads} = k'_{ads} C_A (C_0 - C_{A,ads})$ $r_{desb} = k_{desb} C_{A,ads}^\alpha$ $r_{ads}$, $r_{desb}$ are the adsorption and desorption rates, and $k'_{ads}$, $k_{desb}$ are the adsorption and desorption rate constants. $C_{A,ads}$ is the concentration of adsorbed surface species A. $\alpha$ is the desorption reaction order. $C_0$ is the active site concentration. The units for the active site concentration can be per unit volume reactor or per unit weight powder. $k'_{ads}$ is the adsorption rate constant per active site. With the adsorption rate written using the adsorption rate constant per active site, the active site concentration is separated from the rate constant, and both the active site concentration and the rate constant, as written here, are adjustable kinetic parameters to be fitted.

Equation 1 and its solution are not pressure dependent in the Knudsen flow regime (the Knudsen diffusivity is not pressure dependent) when the adsorbed species concentration is low, $C_{A,ads} \ll C_0$, because then "$(C_0 C_{A,ads})$" in the adsorption rate term is practically $C_0$, which is a constant. However, Equation 1 has an adsorption rate term that is pressure dependent when adsorption gives values of $C_{A,ads}$ larger than about 1% of $C_0$ because $C_{A,ads}$ depends on $C_A$. Then, the mathematical description needs equation 1 to be coupled to the rate equation for $C_{A,ads}$:

$$\frac{\partial C_{A,ads}}{\partial t} = k_{ads} C_A (C_0 - C_{A,ads}) \quad (2)$$

This invention uses the recognition that Equation 1 and its solution change, from being pressure independent, to be pressure (pulse size) dependent when the surface species concentration changes from negligible to substantial (about >1% $C_0$). Since gas pulses of different sizes give different pressures in the powder bed, the measured eluted pulse shape would change with the pulse size to show a pressure dependent process, and vice versa. The invention uses the detection of pulse size dependence and parameter fitting means to simulate the pulse size dependence to determine the active site concentration. The detection of pulse size dependence is performed by injecting gas pulses of different sizes, measuring the eluted pulse shape, and comparing the normalized curves. A two-part parameter fitting process is preferred so that fewer parameters are fitted in each part.

The first part of the parameter fitting is the use of the inert gas response curves to fit and obtain the bed effective diffusivity in the packed bed of the catalyst powder and the pulse sizes. The second part of the parameter fitting process is the use of the reactant response curves to fit and obtain the other kinetic parameters: usually the active site concentration and adsorption rate constant per site, and sometimes also desorption and reaction rate constants. In some situations, it is possible and useful to also include using product response curves in the parameter fitting. The procedure can be easily modified as necessary by those skilled in the art.

The above equations describe the reactor with a nonporous powder. Many catalysts are porous powders with most of the active sites in the pores. In this case, the equations are:

$$\varepsilon_b \frac{\partial C_A}{\partial t} = \frac{1}{A(x)} \frac{\partial}{\partial x} A(x) \cdot D_{e,A}(x) \frac{\partial C_A}{\partial x} - (1-\varepsilon_b) \frac{\partial \overline{q_A}}{\partial t} \quad (3)$$

$$\frac{\partial q_A}{\partial t} = \frac{1}{r^2} \frac{\partial}{\partial r} r^2 D_{par} \frac{\partial q_A}{\partial r} + ads/desb \text{ terms} \quad (4)$$

Equation 3 describes the diffusion of gas A along its flow path, and equation 4 describes the diffusion of gas A inside a porous powder particle in the packed bed. The initial and boundary conditions for equation 3 are the same as for equation 1. The initial and boundary conditions for equation 4 are:

$$0 < r \le r_{par}, t=0, q_A = 0$$

$$r = 0, t \ge 0, -\frac{\partial q_A}{\partial r} = 0$$

$$r = r_{par}, t > 0, q_A = C_A$$

The average concentration in the particles, used in equation (3), is calculated by:

$$\overline{q_A}(x,t) = \frac{3}{4\pi r_{par}^3} 4\pi \int_0^{r_{par}} q_A r^2 dr$$

Where diffusion inside a microporous particle is such that the sorbed molecules are in close proximity to the pore wall because the pores are of molecular dimensions, as in many zeolites, the situation is described as "single phase sorption", and the boundary condition at $r=r_{par}$ should use $q_A=K_c C_A$, where $K_c$ is the Henry constant for the system. Similarly to the non-porous powder, it is also true with a porous catalyst and either a two (gas, adsorbed) phase system or a "single phase sorption" within the catalyst, that the diffusion equations and solution have a pressure relationship as above: the solution changes, from being pressure independent, to be pressure dependent when the sorbed species concentration changes from negligible to substantial. In the latter situation, the mathematical description needs equation 4 to be coupled to the rate equation for $C_{A,ads}$. Then, the detection of pulse size dependence and use of parameter fitting means to simulate the pulse size dependence are also used to determine the active site concentration. In other situations too, the method is similar with suitable modifications to the equations.

For some catalyst powders, it is preferable to detect the shape changes due to a desorbed gas. Then, the measurement should be performed at a temperature where desorption is fast enough for the desorbed gas to produce measurable response curves but not so fast that these resemble inert gas response curves. With many catalysts, adsorption is not activated and this allows the temperature to be chosen according to the desired desorption rate. Usually, this temperature can be determined from a few trial-and-error experiments.

The invention is also useful for measuring the gas diffusivity (intraparticle diffusivity) in a porous powder, $D_{par}$ in equation 4. For this measurement, it is preferred to inject an inert gas pulse that does not adsorb so that the ads/desb term in equation 4 is zero and there will be no pulse size dependence. Then, any pulse size that is small enough to have Knudsen flow conditions can be used. The technique is similar to that above. The response curve that elutes from the packed bed is measured and used with equations 3 and 4 and a parameter fitting routine to extract the gas diffusivity parameter, $D_{par}$.

A two-part parameter fitting is recommended. The first part is to establish a correlation between the bed diffusivity, $D_{e,A}$ in equation 3, and particle size of the powder in the packed bed. This should use a number of packed beds comprising different sized fractions of geometrically similar nonporous particles, e.g. glass beads. For each packed bed of nonporous particles of a fixed size fraction, the response curve data is used to fit its bed diffusivity. By using a number of packed beds of different sized fractions of nonporous particles, a graph of bed diffusivity versus the particle size of the powder in the packed bed is made. This correlation is then used to give the second part of the parameter fitting process a bed diffusivity, based on the particle size of the actual porous powder used, that should be subsequently "quasi-fixed" in the sense that it is only allowed to change in a narrow range of ±10% of the correlation to reflect that a packed bed cannot be exactly reproduced with respect to the packing (void fraction). The second part of the parameter fitting uses the response curves from a packed bed of the porous powder whose intraparticle diffusivity is being measured. Then, for each specific porous powder sample, only one parameter (powder effective internal diffusivity) will need to be fitted, with a second quasi-fixed parameter (bed effective diffusivity) being allowed to change in a range of ±10%.

FIG. 1 shows the schematic of an embodiment 1 apparatus used to measure the active site concentration of a catalyst powder or the gas diffusivity in a porous powder. The apparatus is controlled by a computer 4 and an input/output (I/O) board 5 that form a data acquisition, data treatment, and apparatus control system. I/O board 5 has separate channels for sending TTL on-off voltages to specific electronic switches 6 and separate channels for receiving voltage signals from specific voltage amplifiers that are recorded on the computer after analog-to-digital conversion to digital data. There are four electronically controlled valving means (two of which are shown in FIG. 1, with the other two positioned at 90° to these into and out of the plane of the figure), each of which comprises an electronic switch 6 that controls the passage of current from a voltage supply 7 to a solenoid valve 9. The solenoid valves are placed in a metal block 8 and any one can be used to inject fast gas pulses into a sample tube 30 through the metal block. The gas delivered into sample tube 30 is removed by a gas removing means, which is a vacuum chamber 60 and a vacuum pump 61. The sample tube is attached to the vacuum chamber by a sealing means, which is a sealing block 39.

Vacuum chamber 60 is evacuated by vacuum pump 61, which is preferably a turbomolecular pump with pumping speed larger than 1500 ls$^{-1}$, at its outlet and has two mass spectrometers 70 inside that measure the concentrations in it of the pulsed gases eluted from the sample tube. Each mass spectrometer signal is amplified by a current amplifier 71 and voltage amplifier 72, converted by I/O board 5 and recorded in computer 4 to comprise a gas concentration measuring means. The vacuum chamber is empty except for the mass spectrometers so that there is nothing to block a gas from being pumped away, which is important to prevent extraneous broadening of a response curve.

Figure 2:
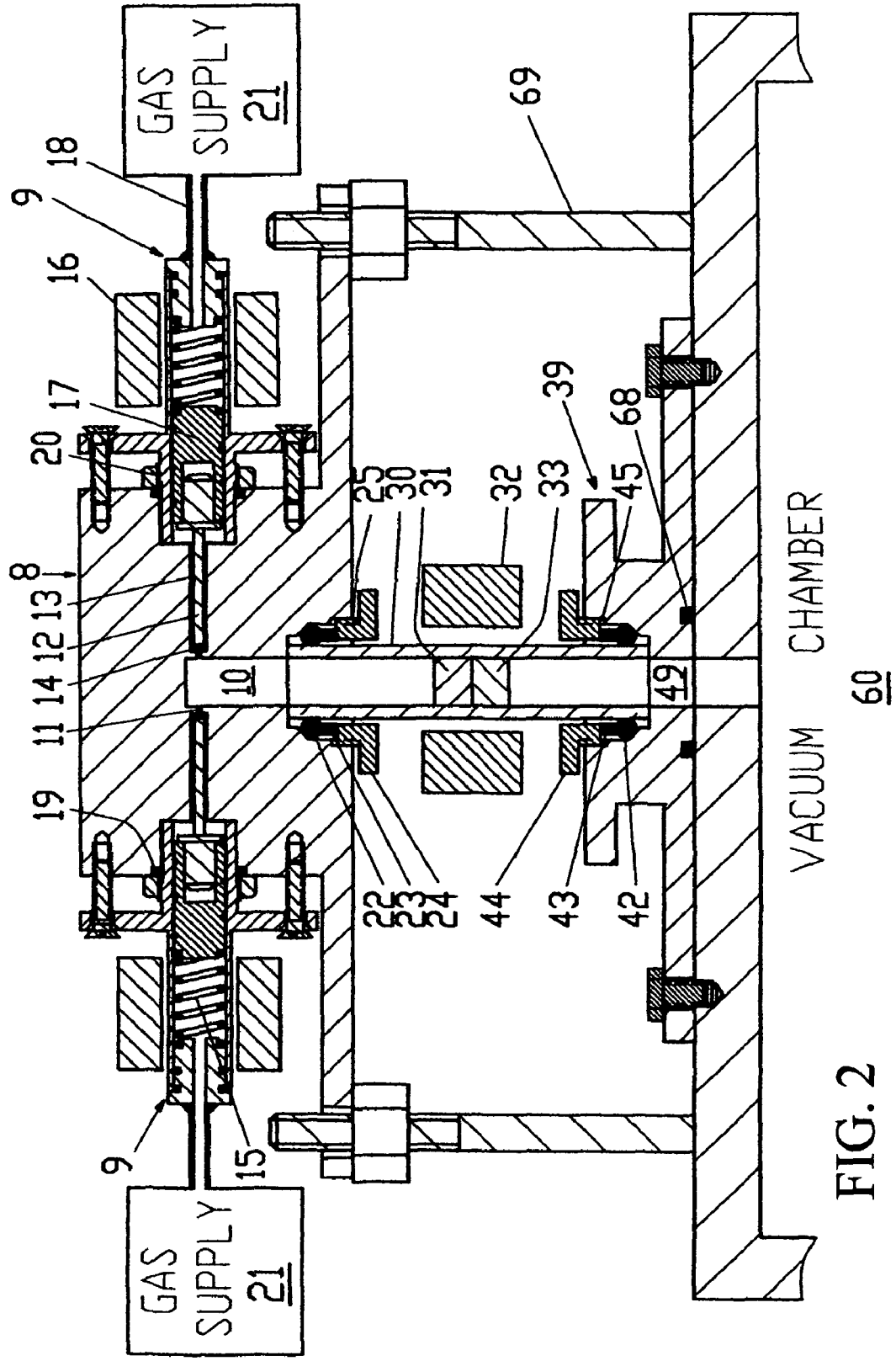
FIG. 2 is a sectional view of the gas flow path part of the embodiment 1 apparatus.

FIG. 2 shows a sectional view of the mechanical components that form the gas flow path of an embodiment 1 apparatus, which mainly consists of the three basic parts: sample tube 30, metal block 8, and sealing block 39. Metal block 8 and sealing block 39 are used to deliver the injected gas pulses from the solenoid valve to the sample tube and to allow the gas pulses to be removed from the sample tube by vacuum chamber 60, respectively. The catalyst powder whose kinetics parameters are being measured is placed as a packed bed 31 in sample tube 30. The packed bed may also include an inert powder to give it a desired length or to improve heat transfer. The packed bed can be heated by a furnace 32 that is controlled by a temperature controller (not shown). When the apparatus is used to measure kinetics parameters other than the gas diffusivity in the catalyst powder, if the adsorption is slow and it is expected that the amount adsorbed will be too small, then an auxiliary packed bed 33 of small particles with a particle size that has a narrow range within the limits 1 and 200 micron, the range preferably between 60 and 90 micron, is placed immediately downstream of packed bed 31 to increase the residence time of the pulsed gas in packed bed 31 to increase the amount adsorbed.

Metal block 8 is mounted on vacuum chamber 60 by two mounting rods 69 and has a cavity 10 to deliver injected gas pulses from an orifice 11 to sample tube 30. Four orifices 11 are spaced at intervals of 90° on the perimeter at the interior end of cavity 10 that are sealed by four solenoid valves 9 (two are shown; the other orifices and valves are positioned at 90° to these into and out of the plane of the figure) installed in metal block 8 to comprise valved openings. Each orifice is sealed by a rubber tip 14 of a solenoid valve 9 in metal block 8. Each solenoid valve 9 is installed in metal block 8 by a sealing means-A 19 and threaded flange 20.

Through any one orifice, a gas or gas mixture can be injected in a radial direction perpendicular to the axis of cavity 10 so that concentration uniformity in the radial direction is more rapidly established. In the case of a momentary pulsed gas injection, the orifice is quickly sealed again so that the gas flow path begins from the interior end of the cavity. Metal block 8 has a polished seat at the open end of cavity 10 to form a seal with an O-ring rubber gasket-A 22 placed on sample tube 30. The metal block delivers the gas injected by the solenoid valve from the interior end of the cavity to sample tube 30. The gas delivery can be either a steady flow or a sequence of gas pulses for pretreating the powder sample or individual pulses of a gas or gas mixture for making experimental measurements.

During a measurement, it is necessary for the delivery of a gas pulse to be fast, preferably less than a millisecond, so that the pulse is very small and the pressure in the flow path is low enough that the gas pulse diffuses by Knudsen flow. The expansion of a high pressure gas pulse to the low pressure needed for Knudsen flow is best carried out in a large void space. Furthermore, to get faster gas diffusion at low pressure, the flow path should have a large radial dimension and a small axial dimension. Metal block 8 is directed towards these dimensions since it provides a wide and shallow cylindrical cavity 10 for the flow path. The volume of the cavity is larger than 0.1 ml. This makes this device different from and superior to prior art devices that all seek to minimize the volume by using narrow bore channels. Cavity 10 is empty, that is, the cavity is smooth-walled and hollow so that all space within the cavity lie in line-of-sight of sample tube 30 placed at the open end of the cavity. This further differs from and improves on prior art devices that seek to promote mixing with a mixing chamber with solid objects or obstructing protrusions.

Gas injection is by the action of a valving means or pulsed valving means, that is, means for injecting gas or pulsed injecting of gas. The valving means can be a leak valve that injects a steady flow gas delivery or, as here, an electronically controlled solenoid valve that injects either a steady flow or pulsed gas delivery. The pulsed valving means is an electronically controlled solenoid valve that injects a pulsed gas delivery. Each solenoid valve 9 comprises a soft iron piece 17 that holds a valve stem 12 positioned in a stem channel 13, a spring 15 that presses on the valve stem to seal an orifice 11 by pressing a rubber tip 14 in the valve stem against the orifice, and a solenoid 16. The walls of the orifice openings are thin but with sufficient thickness to resist deformation when spring pressure is applied. When computer 4 uses I/O board 5 to send an "on" TTL-signal to turn an electronic switch 6 "on", the electronic switch opens to let voltage supply 7 send a current through the particular solenoid 16 that the switch controls. The current in the solenoid produces a magnetic force that pulls out soft iron piece 17 of the valve and opens the orifice. When computer 4 uses I/O board 5 to send an "off" TTL-signal to turn the electronic switch 6 "off", it shuts off voltage supply 7 from the solenoid, the solenoid's magnetic field fades and the spring pushes on the valve stem to close the orifice.

In the case of a momentary pulsed gas injection, the pulse size is controlled by the time that the TTL-signal to a specific electronic switch 6 is "on", which is the time when it lets a current flow from voltage supply 7 to its particular solenoid. Sharp gas pulses need short on-times of less than about a millisecond. An over-voltage of about 100 V is used for the nominal 24 V solenoid to give a faster opening of the valve when measurements are made. A threaded flange 20 is used to adjust the spring strength of spring 15 so that it just forms a gastight seal with rubber tip 14 without over-tightening of the spring. Gases are supplied to each of the valves through a tubing 18 from a gas supply 21. When a gas pulse is injected, the gas momentarily flows through orifice 11 and expands to a low pressure in cavity 10. The gas then diffuses through sample tube 30, packed bed 31 (and auxiliary packed bed 33 if that is used), sealing block 39 and vacuum chamber 60, and is evacuated by vacuum pump 61.

The open end of cavity 10 has a polished seat for O-ring rubber gasket-A 22 fitted around the upstream end of sample tube 30. A gastight seal is made by the compression of the O-ring rubber gasket using a threadpiece-A 24 and a threaded means-A 25 to press onto a stainless steel ring-A 23. Threadpiece-A 24 is notched on the exterior face to let a L-shaped screwdriver apply a torque tightening force. Sample tube 30, cavity 10, and conduit-D 49 have a similar internal diameter and form a cylinder to simplify the mathematical description of the device.

The downstream end of sample tube 30 is attached by an O-ring seal to sealing block 39. The top of sealing block 39 has a polished seat for an O-ring rubber gasket-B 42 fitted around the downstream end of sample tube 30 and a gastight seal is made by its compression using a threadpiece-B 44 and threaded means-B 45 to press onto a stainless steel ring-B 43. Threadpiece-B 44 is notched on the exterior face to let a L-shaped screwdriver apply a tightening force. Sealing block 39 is sealed onto vacuum chamber 60 by an O-ring rubber gasket at a sealing means-B 68.

Vacuum chamber 60 has two mass spectrometers 70 (shown in FIG. 1 but not shown in FIG. 2) to measure the gas concentrations in the vacuum chamber. In some other apparatus, more mass spectrometers can be used. The mass spectrometers are positioned so that their ionization zones are aligned with the reactor outlet. Since the mass spectrometers are also used to measure a pulsed signal with a short rise time, they should have an amplifier bandwidth larger than 100 Hz. Such mass spectrometers are more expensive, and an alternative is to use a cheaper mass spectrometer, e.g. Model RGA 200 quadrupole mass spectrometer from Stanford Research Systems Company, Calif., and a modification that allows the measurement of the electron current from the electron multiplier of the mass spectrometer with a fast response current amplifier 71, e.g. Keithley Model 428 with a selectable range of amplification, including the range $10^{-11}$ A/V with a bandwidth of 1400 Hz. Narrow response curves have to be recorded with a range with a large enough bandwidth. For increased sensitivity, the output voltage signal from current amplifier 71 can be further amplified by voltage amplifier 72 whose output is sent to I/O board 5. The mass spectrometer sensitivity is selectable and a usual sensitivity is 0.2 A/torr. If necessary, a higher sensitivity can be used at the expense of a shorter lifetime for the electron multiplier. If the mass spectrometer is a type that has a sufficiently fast amplifier, its amplifier's output voltage can be sent directly to I/O board 5 and there is no need to use a current amplifier 71 and voltage amplifier 72.

The method of performing a measurement is now described:

(1) Gas preparation.

The solenoid valve that is to be used for providing gas pulses is prepared with a reactant(s) and inert gas mixture in about 8:2 ratio for an active site concentration measurement or with an inert gas for a gas diffusivity measurement. If the sample needs cleaning, one of the other valves is prepared with the cleaning gas.

(2) Sample preparation.

Sample tube 30 is removed from the apparatus as follows: loosen threadpiece-A 24 and lift metal block 8 off and away from the sample tube, remove O-ring rubber gasket-A 24, stainless steel ring-A 23, and threadpiece-A 24 from the sample tube, lift furnace 32, loosen threadpiece-B 44 and lift the sample tube off sealing block 39, remove O-ring rubber gasket-B 42, stainless steel ring-B 43, and threadpiece-B 44 from the sample tube, and remove the sample tube. The amount of catalyst powder to be placed in the sample tube is determined by the largest pulse size that can be used and still satisfy the condition for Knudsen flow.

The notion of satisfying the condition for Knudsen flow means that the pressure must be low enough, which puts an upper limit on the pulse size. The upper limit is usually determined experimentally using inert gas (e.g. Ar) response curves of different size pulses. It is the pulse size where the normalized shape begins to differ (generally sharpened) from the normalized shapes of smaller pulses (an example is curve Z1 in the inset in FIG. 5A). With this embodiment and a 4 mm inner diameter (i.d.) sample tube, experiments showed that the upper limit is $2.0 \times 10^{15}$ molecules per pulse, that is, pulse sizes smaller than this are needed to satisfy the condition for Knudsen flow.

For an active site concentration measurement, the upper limit on the amount of catalyst powder that can be used in the sample tube is determined by that when using the largest gas pulse useable (and still have Knudsen flow), the adsorbate has to occupy a large enough fraction (>1%) of the active sites to cause the (adsorbate) response curve to be measurably different from that response curve where a negligibly small fraction of the active sites was occupied. Using the value of $2.0 \times 10^{15}$ molecules per pulse for the largest gas pulse useable, if the feed gas is 80% adsorbate and the adsorption rate is fast and all pulsed adsorbates are adsorbed, the maximum amount of catalyst in the sample tube is that with less than $2.0 \times 0.8/0.01 \times 10^{15} = 1.6 \times 10^{17}$ active sites. This can be put into a more conventional unit using a typical areal atomic density as $1.5 \times 10^{19}$ atoms/m$^2$, a catalyst powder has 10 m$^2$/gm, and assuming 10% of surface atoms are active sites, which gives $1.5 \times 10^{19}$ active site per gm. In this case, the maximum amount of catalyst that can be placed in the sample tube is only 10 mg.

If more catalyst was used, the highest occupied site fraction will be less than 1%, with a response curve that will be indistinguishable from the response curves where a smaller fraction of the active sites was occupied. Actually, even less catalyst powder should be used because the experiment cannot use a situation where all adsorbates get adsorbed as this will result in there being no response curve; generally, it is advisable to have adsorbed no more than 85% of the absorbable gas. If the catalyst and adsorbate are such that the adsorption rate is too slow for all the pulsed adsorbates to be adsorbed, the catalyst amount should be less in order that the occupied active site fraction is >1%. This invention is novel in the use of a very small amount of catalyst powder to produce response curves that can be used to determine the active site concentration.

The above paragraph considers the situation where the adsorption stoichiometry is one adsorbate molecule to one active site. There can be situations where the adsorption stoichiometry is different. Those skilled in the art can easily adapt the calculation. For example, oxygen adsorbs dissociatively and each oxygen molecule gives two adsorbate fragments. Here, an "adsorbate fragment" means an adsorbed species that occupies one active site. In this case, the upper limit on the amount of catalyst in the sample tube is that with $2.0 \times 0.8/0.01 \times 2 \times 10^{15} = 3.2 \times 10^{17}$ active sites in order for the surface concentrations to be >1% the active site concentration. In actual practice, even less catalyst should be used so that the changes in the response curve are more salient. The upper limit on the amount of catalyst powder in the sample tube is where the number of adsorbate fragments in the largest gas pulse useable (and still have Knudsen flow) occupy 1% of the active sites present, that is, the number of active sites on the catalyst powder must be less than 100 times the number of adsorbate fragments in the largest gas pulse that is sufficiently small to satisfy the condition for Knudsen flow. For good parametric sensitivity, it is better for the number of active sites on the catalyst powder to be one-tenth to one-hundredth of this. It should be understood that since the object is to measure the active site concentration, this will not be known initially. The use of the calculation is to guide a user with an estimate of the amount of catalyst powder to place in the sample tube, which can then be adjusted according to the experimental results. For example, if the adsorbate response curves do not change with pulse size, it is probable that there is too much catalyst powder in the sample tube, and the next experiment should use less catalyst powder. In cases where adsorption is too slow, it may be better to use an auxiliary packed bed of small inert particles, preferably about 80 micron, placed downstream of the packed bed to increase the residence time of the adsorbate in the sample tube, rather than using more catalyst powder.

For an active site concentration measurement, the lower limit on the amount of catalyst powder used in the sample tube is determined by that when using the smallest gas pulse useable (determined by the type of solenoid valve, and is about $3.0 \times 10^{12}$ molecules per pulse here), the adsorbate should not occupy all the active sites, and should occupy <50% the active sites. This lower limit is small enough that it cannot be practically exceeded, and is not considered further.

The above numbers can be used to estimate in alternative embodiments the amount of active sites to be placed in the sample tube as follows. It is assumed that the gas pulse expands to pressure equilibrium in the void space in front of the packed bed, and pressure equilibration is fast so that almost no gas has flowed into the packed bed. In this embodiment, the void space is a cylinder 4 mm i.d. and 30 mm long, which is a volume of 0.38 ml. When $2 \times 10^{15}$ molecules are injected, the initial pressure in the void space is 0.15 torr. Thus, it is assumed that the pressure should be less than 0.15 torr to meet the condition for Knudsen flow. This pressure also depends on the dimensions of the void space and particles in the packed bed; it can be different in other apparatuses where the dimensions are different. Thus, the guideline for the maximum amount of active sites that can be placed in the sample tube is that 1% of it is equal to the number of adsorbate fragments in the pulse that when injected gives a pressure of 0.15 torr in the void space. For god parametric sensitivity, it is advisable to use less, one-tenth to one-hundredth, of this maximum amount in an initial experiment. It should be understood that this is only a rough estimate. The upper limit pulse size useable and catalyst amount to be placed in the sample tube is preferably determined experimentally as described above.

For the instance of a 1% metal loading supported catalyst, a rough calculation based on the loading and assuming 80% exposed atoms indicates that about 5 mg of catalyst powder is needed. A trial-and-error iterative measuring procedure can also be used to estimate the amount of catalyst powder to be placed in the sample tube. A precisely weighed amount (about 50 mg) of catalyst is mixed with a precisely weighed amount (about 500 mg) of support. A precisely weighed amount (about 50 mg) of the mixture is placed in sample tube 30 as a packed bed 31 held in place by wire meshes. For a gas diffusivity measurement, it is useful to first perform some simulations to determine the length of packed bed that should be used to have good parameter fitting sensitivity, then place a weighed amount of the porous powder that will give approximately this length in sample tube 30 as a packed bed 31 held in place by wire meshes. The length of the packed bed is measured and the sample tube is installed on the apparatus by reversing the steps of its removal to have the outlet end of sample tube 30 sealed to the sealing block, furnace 32 positioned to surround packed bed 31 using a mounting rod (not shown), and metal block 8 sealed to the inlet end of the sample tube, with metal block 8 positioned using mounting rods 69. Many gas diffusivity measurements can be carried out at room temperature, in which case, furnace 32 is left out.

(3) Catalyst pretreatment.

The vacuum chamber is evacuated. If the catalyst requires a cleaning pretreatment, pulses of the cleaning gas are delivered into the packed bed and removed through the vacuum chamber, while furnace 32 is used to keep the packed bed at a set temperature. The gas pulsing is continued for a set time at a set rate of pulsing. Then, with the packed bed at a suitable desorption temperature, evacuation by the vacuum chamber is continued for a time sufficient to desorb the cleaning gas and provide a vacuum in the sample tube.

(4) Measurement.

The procedure is slightly different for active site concentration measurement and gas diffusivity measurement as follows:

(a) Active site concentration measurement: The furnace is set to a suitable temperature. Many gas adsorption processes are not activated, in which case the adsorption temperature can be any convenient temperature. The measurement comprises the pulsing of different size gas pulses, where the largest and smallest pulses should differ by at least ten-fold. It is preferable that the range be from $1 \times 10^{13}$ to $1 \times 10^{15}$ molecules per pulse, and in some other designs, it may be possible to have it from $1 \times 10^{12}$ to $1 \times 10^{17}$ molecules per pulse. If the adsorbed gas dissociates, the catalyst has to be cleaned after each pulse, which is performed as described in step (3) above. For an adsorbed gas that is not dissociated, desorption by evacuation at an appropriate temperature can be used to clean the sample. During the pulsing of each gas pulse, the concentrations of eluted reactant gas and inert gas in the vacuum chamber are measured using the mass spectrometers to give the response curves as described in the example below.

(b) Gas diffusivity measurement: Many gas diffusivity measurements can be carried out at room temperature, but if a different temperature is required, the furnace is used and set to the required temperature. The measurement comprises the pulsing of gas pulses, with the size of the gas pulses kept between $1 \times 10^{13}$ and $1 \times 10^{15}$ molecules per pulse. During the pulsing of the gas pulse, the concentration of the eluted gas in the vacuum chamber is measured using the mass spectrometers to give the response curve as described below. If the signal-noise ratio of the response curve is poor, the response curves from many (e.g. five) pulses can be signal averaged to improve the quality of the curve. In this measurement, the length of the catalyst powder packed bed is important. It has to be long so that the pulse stays in the packed bed long enough to avoid the situation that just a small fraction of the pulse gets into the pores that changes the response curve only by an indistinguishable tail, but it must not be too long that the pulse stays in the packed bed for too long and gives a constant concentration in the pores. Generally, due to the first consideration, the length of the packed bed should be at least 7 mm, and due to the second consideration, the length should be sufficiently short so that the bed diffusion time constant is less than the intraparticle diffusion time constant in the catalyst powder. The way to estimate these time constants is given in the example below.

The response curves (concentrations of eluted reactant gas and inert gas in the vacuum chamber versus time) are measured using the mass spectrometers as follows. The mass spectrometer signals are very small electron currents from the electron multipliers that are converted and amplified by current amplifiers 71 and voltage amplifiers 72 to volt-range voltage signals. Computer 4, using I/O board 5, receives and records the voltage signals and produces the response curves. The response curves are synchronized by the computer using the signal that turns an electronic switch 6 to "on" as the reference or zero time.

The pulse sizes are controlled by the on-time of an electronic switch 6 using a previously established correlation of pulse size with on-time and operator experience. Sharp gas pulses need short on-times of about 1 ms. The control of the pulse size by the on-time is a rough guide for setting the on-time of the electronic switch. The pulse size actually injected is calculated from the area of the eluted inert gas response curve. The pulse size should be calculated from the area of a net gas flux versus time curve, but the response curve, which is a gas concentration versus time curve, can be used if it has been calibrated for the pulse size. In some other apparatuses with a vacuum pump with a higher pumping speed, >3000 $ls^{-1}$, the mass spectrometer signal gives a response curve that is a net gas flux versus time curve.

The shapes of the response curves are the primary data. The response curves are more easily compared as normalized curves, but the parameter fitting routine used to extract the active site concentration should use the non-normalized curves. The parameter fitting is carried out using a mathematical description of the Knudsen flow of the gas pulse from its input at the interior end of cavity 10 to its evacuation at the vacuum pump that contains the active site concentration or gas diffusivity as a parameter. An example of this is the mathematical description given above as equations 3 and 4 with the boundary conditions and rate expressions, in which $C_0$ is the active site concentration parameter or $D_{par}$ is the gas diffusivity parameter. The particular equation, boundary conditions and rate expressions depend on the actual structure of the apparatus and can be different in different apparatuses.

The mathematical equation(s) is solved by a computer using a standard numerical analysis method, e.g., the finite volume method and Crank-Nicholson algorithm described in numerical analysis texts. The solution is used to calculate and plot the response curves of the pulsed gases at the measurement points (mass spectrometer ionizers) in the vacuum chamber. The first calculation will usually give calculated response curves that do not fit the measured response curves well. The adjustable parameters are adjusted until the calculated response curves fit the measured response curves well, at which point the active site concentration parameter or the gas diffusivity parameter is the desired measured quantity. The adjustable parameters can be adjusted by noting how the calculated response curves differ from the measured response curves and using operator experience to change the magnitude of the parameters. Alternatively, an optimization technique, e.g. the Nelder-Mead algorithm described in parameter estimation texts, can be used and the parameter fitting automated.

In the measurements, two needs must be met: (1) the injected gas pulse must have a pulse width less than a fourth that of the gas response curve, and (2) for porous powders, for active site concentration measurement, the diffusion time constant of the packed bed should be larger than the diffusion time constant into the interior of the particles of powder sample, while for gas diffusivity measurement, it is vice versa. The first need is because the shape and pulse width (time duration of the full width at half maximum) of injected pulses are not consistently reproducible since they depend on many physical conditions in the solenoid valve that cannot be controlled. However, the effect of the shape and time duration of the injected pulse will be unimportant if the pulse width of the response curve is much larger than (more than four times) that of the injected pulse, although it is also not advisable to have the pulse width of the response curve too large (e.g. >10 s) because that makes it harder to detect changes. The second need, in the instance of an active site concentration measurement, is to ensure that the time taken by the gas pulse to diffuse through the packed bed is long enough so that the gas has sufficient time to diffuse into the interior of the particles of powder sample, while in the instance of a gas diffusivity measurement, it is to ensure that the time taken by the gas pulse to diffuse through the packed bed is not too long so that the gas does not have sufficient time to come to a constant concentration in the interior of the powder.

Using the solenoid valve described, the injected pulse widths are in the range 0.5 to 0.8 ms, which determines that the width of the response curve should be more than 4 ms. Since the usual width of the response curves are more than 4 ms, the question of the first need in the above paragraph does not need to be further considered. The time constant for diffusion in porous particles can be approximated by $t_{diff} = r_p^2/D_{par}$, where $r_p$ is the hydraulic radius of the powder and $D_{par}$ is the intraparticle gas diffusivity. In the instance of an active site concentration measurement, the amount of catalyst used in the sample is to contain less than $1 \times 10^{16}$ active sites, and usually this amount by itself will only give a very short packed bed that does not satisfy the second need above. Then, the powder should be mixed with an inert powder that has a similar bed effective diffusivity to give a packed bed of the desired length. The time constant for diffusion in the packed bed can be approximated by $t_{bed} = l_b^2/D_{bed}$, where $l_b$ is the length of the packed bed and $D_{bed}$ is the bed effective diffusivity. These diffusion time constants can be adjusted using different ratios of mixing with an inert powder, different sized particles, or by using a composite packed bed that has a aft or aft and fore packed bed of a smaller particle inert material such that the diffusion time constant of the composite packed bed is large enough. In the instance of a gas diffusivity measurement, these time constants should be such that $t_{bed} < t_{diff}$, and the amount of catalyst used should be chosen to give a length of packed bed consistent with this. In doing this, the calculation of $t_{diff}$ needs the magnitude of $D_{par}$, which is the quantity being measured, and a trial-and-error process with initially an estimated $D_{par}$ may be used to find a suitable length of packed bed.

Detailed Description of Embodiment 2

Figure 3:
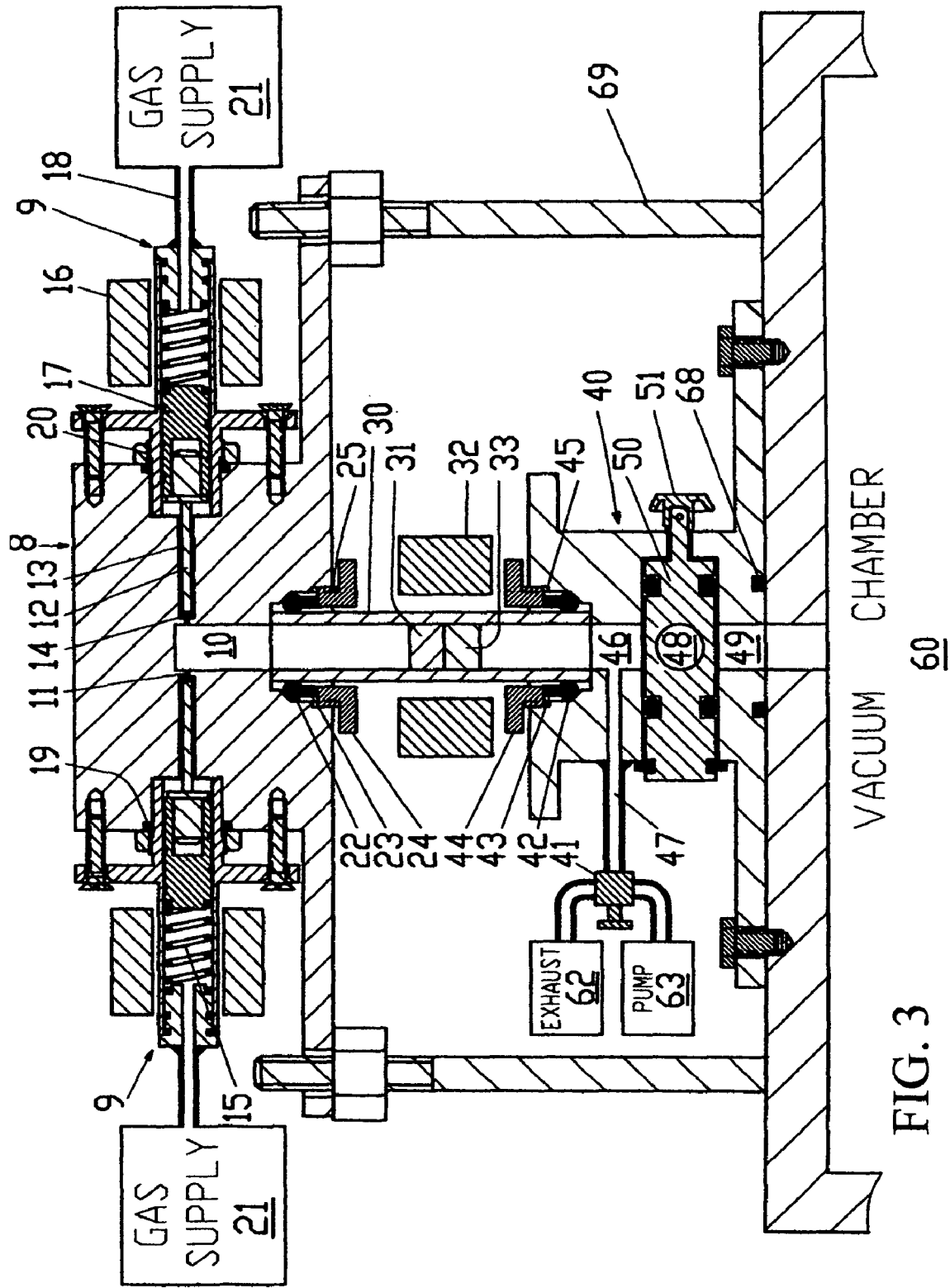
FIG. 3 is a sectional view of the gas flow path part of an embodiment 2 apparatus.

FIG. 3 shows a sectional view of the mechanical components that form the gas flow path of an embodiment 2 apparatus. The embodiment 2 apparatus is designed particularly for use with a catalyst powder that needs cleaning by a continuous flow of cleaning gas at atmospheric pressure. The embodiment 2 apparatus is basically similar to the embodiment 1 apparatus and only its differences are described. The embodiment 2 apparatus is different in that different gas removing means, namely, vacuum chamber 60 and vacuum pump 61 or exhaust 62 or roughing pump 63, can be selected using a sealing block-A 40 that is different from sealing block 39. Sealing block-A 40 is different in being able to provide for the outlet from the sample tube to be selected to communicate with either vacuum chamber 60 or through a 3-way ball valve 41 to an exhaust 62 or a roughing pump 63.

Sealing block-A 40 is used to deliver the gas from the sample tube to one of the gas removing means, that is, either vacuum chamber 60 or exhaust 62 or roughing pump 63. Sealing block-A 40 is also used to isolate the sample tube from the vacuum chamber when it is desired to use a gas at atmospheric pressure to clean the powder in the sample tube. During a measurement when gas pulsing is used, sealing block-A 40 is used to let the gas diffuse from sample tube 30 to vacuum chamber 60 by evacuation. During a cleaning when a steady gas flow is used, sealing block-A 40 is used to isolate the vacuum chamber and the gas is removed through three-way valve 41, which is positioned to open towards exhaust 62.

The outlet end of sample tube 30 is attached by an O-ring seal to sealing block-A 40. The top of sealing block-A 40 has a polished seat for an O-ring rubber gasket-B 42 fitted around the outlet end of sample tube 30. A gastight seal is made by the compression of O-ring rubber gasket-B 42 using a threadpiece-B 44 and a threaded means-B 45 to press onto a stainless steel ring-B 43. Threadpiece-B 44 is notched on the exterior face to allow a L-shaped screwdriver to apply a tightening force. Sealing block-A 40 is sealed onto vacuum chamber 60 by an O-ring rubber gasket at a sealing means-B 68.

Sealing block-A 40 and three-way ball valve 41 comprise the means to switch the sample tube to communicate with either vacuum chamber 60 or exhaust 62 or roughing pump 63. Sealing block-A 40 has flow paths comprising either (a) conduit-A 46 and a much narrower conduit-B 47 that leads to three-way ball valve 41, which is connected further to tubings that lead to exhaust 62 or roughing pump 63, or (b) conduit-A 46, conduit-C 48 in a rotary plug 50 that is rotated by a handle 51 to form an on-off valve between the sample tube and the vacuum chamber, and conduit-D 49 to vacuum chamber 60. Rotary plug 50 can be those in rotary plug valve 4F-PR4-VT-SS manufactured by the Parker Hannifin Corporation, Instrumentation Valve Division, Jacksonville, Ala. Conduit-B 47 (not shown with a correct scale in FIG. 3) is much narrower than conduit-A 46, conduit-C 48, and conduit-D 49 so that when rotary plug 50 is turned "on" to have these latter three conduits aligned, almost all the gas will flow into vacuum chamber 60. In some other apparatus, the function of sealing block-A 40 and three-way ball valve 41 can be made from a switching valve, e.g. a five-way ball valve.

The method of the embodiment 2 apparatus differs from the method of embodiment 1 in further providing for the cleaning of the catalyst powder with a flowing gas at atmospheric or higher pressure. The difference in the catalyst pretreatment and measurement steps are described using the same instance of a 1% metal loading supported catalyst:

(1) Gas preparation.

This step is the same as in embodiment 1.

(2) Sample preparation.

This step is the same as in embodiment 1, except that there is sealing block-A 40 in place of a sealing block 39.

(3) Catalyst pretreatment.

Rotary plug 50 in sealing block-A 40 is turned "off" to isolate the vacuum chamber from the sample tube. The vacuum chamber is evacuated. Three-way ball valve 41 is turned to exhaust 62. A pretreatment to clean the catalyst in the packed bed is performed. For catalysts that do not need it, this can be omitted. Usually, the sample pretreatment requires a flowing gas at atmospheric pressure, although some catalysts can be cleaned by gas pulses. Pretreatment gas at about 5 cc/min flow is supplied by a solenoid valve operated for steady flow gas delivery through one of the orifices 11. Furnace 32 is used to heat the packed bed at a set temperature. The gas flow is continued for a set time. Then, the gas supply is stopped and three-way ball valve 41 is turned to roughing pump 63 to evacuate the sample tube for a few seconds. The three-way ball valve is turned to "off" and rotary plug 50 in sealing block-A 40 is turned to communicate the sample tube with the vacuum chamber. Then, with the packed bed at a suitable desorption temperature, evacuation of the sample tube is continued using the vacuum chamber for a time sufficient to desorb the pretreatment gas from the catalyst.

(4) Measurement.

This step is the same as in embodiment 1, except that if the adsorbed gas dissociates and the catalyst has to be cleaned by a flowing gas after each pulse, the cleaning is performed as described in step (3) above.

Detailed Description of Embodiment 3

A novel aspect of this invention, in the performance of an active site concentration measurement, is that a gas pulse in Knudsen flow is used to provide a surface concentration that is both a measurable fraction of, roughly >1%, and substantially less than, roughly <50%, the active site concentration. Experiments have shown that the need to keep the flow in Knudsen flow in the above two embodiment requires pulse sizes to be less than $2 \times 10^{15}$ molecules per pulse. Then, to keep the surface concentration substantially less than the active site concentration, the amount of catalyst in the sample should contain about less than $1 \times 10^{16}$ active sites. This amount of active sites is quite small, e.g., for a 1 wt % Pt catalyst with 80% metal dispersion, this is the amount of active sites present in about 5 mg catalyst powder. Then, to satisfy that the bed diffusion time constant (for flow in the packed bed) be larger than the intraparticle diffusion time constant in the catalyst powder (for flow inside the powder), the two embodiments above have to use a packed bed of a mixture of catalyst and inert powders. However, in some measurements, there may be no suitable inert powder to use to make a mixture. Then, to satisfy the required relative magnitudes of the two diffusion time constants, it will be necessary to use a large amount of powder. But with such a large amount of catalyst powder, the constraint on the largest pulse size that can be used and still keep in Knudsen flow in the above two embodiments will result in there being too small a surface concentration such that the changes in the reactant response curves will be too small to measure. Embodiment 3 is designed for use with these catalysts to allow the use of bigger pulse sizes, which are big enough to allow the amount of catalyst powder used to contain up to $2.5 \times 10^{17}$ active sites.

Figure 4:
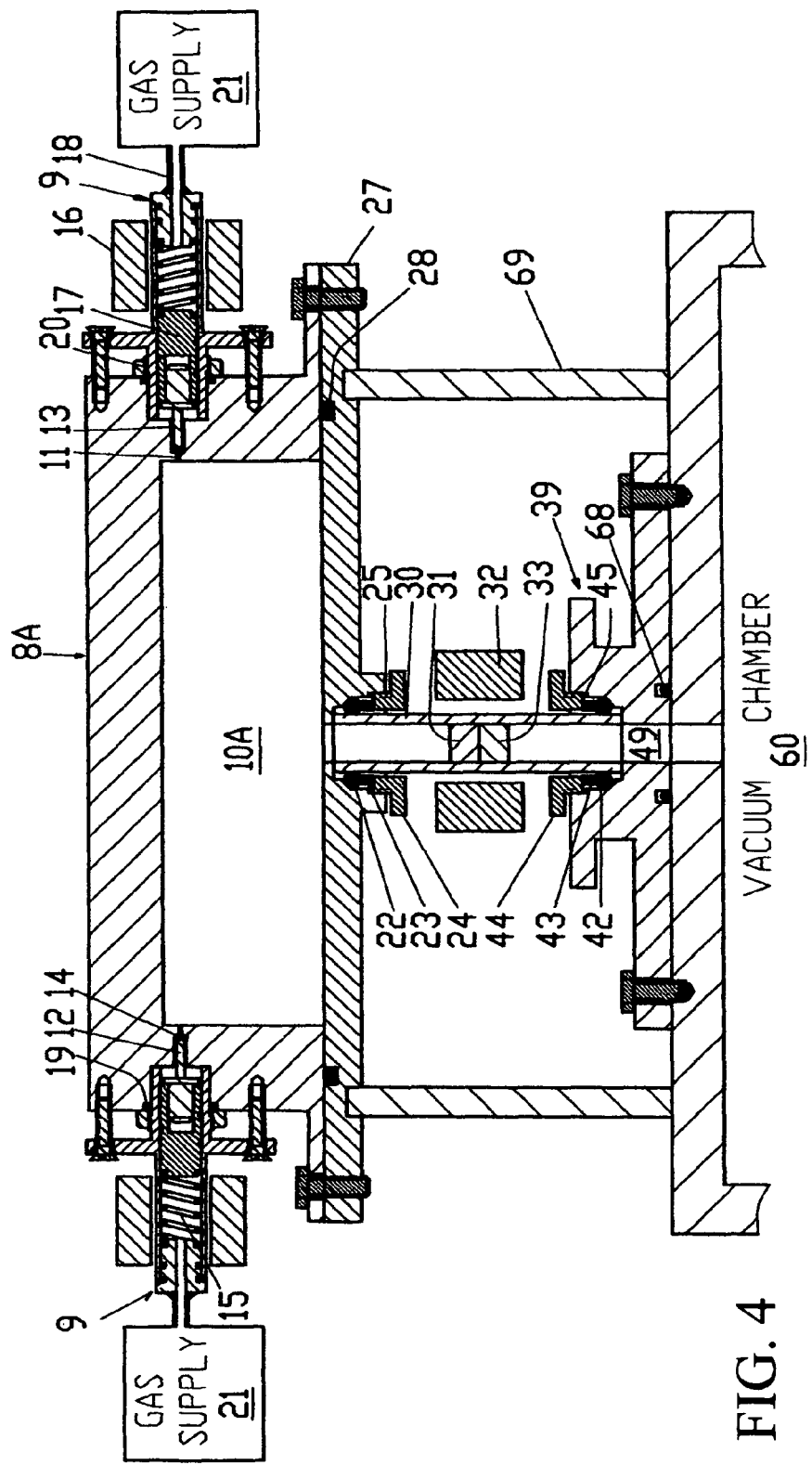
FIG. 4 is a sectional view of the gas flow path part of an embodiment 3 apparatus.

FIG. 4 shows a sectional view of the mechanical components that form the gas flow path of an embodiment 3 apparatus. The embodiment 3 apparatus is designed particularly for when it is necessary to use a large amount of catalyst powder in the sample tube. Only the difference between the embodiment 3 and embodiment 1 apparatuses is described here. The difference is in the different size of cavity 10A in metal block 8A, that is, cavity 10A is much larger than cavity 10 in metal block 8 in embodiment 1. Cavity 10A has a volume that is at least 0.1 ml, and it is preferred to have it larger than 0.5 ml, and it can be as large as 50 ml.

Metal block 8A is sealed onto a metal plate 27 by a sealing means-C 28. Metal plate 27 is mounted onto vacuum chamber 60 by two mounting rods 69. Metal block 8A, like metal block 8, is directed towards providing a wide and shallow cylindrical cavity 10A to deliver the gas from orifice 11 to sample tube 30, and to lower the pressure to provide for Knudsen flow in the case of pulsed delivery. It is similarly different from and superior to prior art devices that all seek to minimize the volume by using narrow bore channels. Cavity 10A is empty, that is, the cavity is smooth-walled and hollow so that, although some space within the cavity is not in line-of-sight of sample tube 30 placed at the open end of the cavity, gas molecules can exit the cavity with less wall collisions. This further differs from and improves on prior art devices that work on the principle to provide mixing during gas delivery with a mixing chamber, added solid objects, or obstructing protrusions. Although sample tube 30 and cavity 10A do not have a similar internal diameter, they have cylindrical symmetry to simplify the mathematical description of the device.

Due to the much larger volume of cavity 10A, which can be by up to about a factor of fifty larger than the cavity in embodiment 1, the pulse size that can be used and still satisfy the condition for Knudsen flow is bigger, and can be as large as $1 \times 10^{17}$ molecules per pulse. Then, to satisfy that a gas pulse should occupy a substantial fraction of the active site concentration, the amount of catalyst in the sample can contain more sites, e.g. $2.0 \times 10^{17}$ active sites. Thus, the embodiment 3 apparatus is basically different from the embodiment 1 apparatus in the use of a much larger amount of catalyst powder, e.g. about >100 mg catalyst. During measurement, the amount of powder catalyst used is chosen to give a required length of packed bed, and there is no need to use dilution with an inert powder to reach the required length. To those skilled in the art, it is also clear that for use with a catalyst powder that needs cleaning by a flow of cleaning gas at atmospheric pressure, an alternative embodiment can be constructed by the use of the sealing block-A 40 of embodiment 2 in place of the sealing block 39.

Catalyst Sites Measurement: Example

The catalyst powder in this example is a vanadium and molybdenum-based $SiO_2$-supported mixed oxide catalyst for the selective oxidation of ethane for which the concentration of defect sites for oxygen adsorption is to be measured. Prior to the measurement, the catalyst was dried at 120° C. overnight and then calcined in air at 350° C. The oxygen adsorption active site density of the catalyst was first estimated. Based on previous activity measurements and the catalyst composition, this was estimated to be $2.5 \times 10^{17}$ sites/gm catalyst. The catalyst particles were sieved to the 140-200 mesh fraction, which is an average radius of $r=0.042$ mm. The $SiO_2$ support is a porous powder with an average pore size of 6.5 nm (from BET measurement). Its intraparticle effective diffusivity for Ar had been previously measured to be $D_1=1.5 \times 10^{-8}$ m²/s. The time constant for intraparticle diffusion (diffusion in the porous particles) can be approximated by $t_1=r^2/D_1$, which gives $t_1=0.12$ s. Thus, to perform a measurement without intraparticle diffusion limitation, the time constant for diffusion in the packed bed (axial diffusion time constant) should be larger than 0.12 s. Previous experiments with powder particles of the size here gave the bed effective diffusivity for Ar as $D_2=3.5 \times 10^{-5}$ $d_r$ m²/s, where $d_r$ is the internal diameter (i.d.) of the packed bed (4 mm here). The time constant for diffusion in the packed bed can be approximated by $t_2=l^2/D_2$, where l is the length of the packed bed. Since the criterion requires that $t_2$ should be larger than 0.12 s, this therefore determines that l should be 7 mm or longer.

If embodiment 1 or 2 of this invention is used and adsorption was very fast, it is estimated that the packed bed should contain no more than $3.2 \times 10^{17}$ sites, but previous experiments indicated that the adsorption on this catalyst is quite slow and the actual amount has to be much less, preferably it should contain about $2.0 \times 10^{14}$ sites. To form a packed bed that has the length of 7 mm, from previous experiments using the tube of i.d. 4 mm, it is estimated that 70 mg of powder are needed. Also, from the estimated site concentration of $2.5 \times 10^{17}$ sites/gm catalyst, in order for the packed bed to contain $2.0 \times 10^{14}$ sites, it should have 0.8 mg catalyst. Thus, there are two requirements to be satisfied for the packed bed: it should have 70 mg powder and 0.8 mg catalyst, which is satisfied by using a mixture of catalyst and $SiO_2$ support, where the $SiO_2$ support is a diffusively similar inert powder that is added to get the packed bed to a sufficient length so that the bed diffusion time constant is larger than the intraparticle diffusion time constant in the catalyst powder.

Since it is difficult to measure accurately the small amount of 0.8 mg, about 20 mg catalyst was precisely measured and mixed with about 1.75 g of precisely measured $SiO_2$ support to get the correct ratio mix of catalyst and $SiO_2$ support. It is preferable for the catalyst and support to be sieved to the same particle size, and to use a small mesh range to get a narrow size distribution. Then, about 70 mg of the mixed powder was precisely measured and placed in a sample tube 115 mm long and 4 mm i.d. to form a packed bed about the middle of the tube held in place by a 250 mesh stainless steel screen. The length of the packed bed was measured. The dimensions of the sample tube can be different.

If embodiment 3 of this invention is used, the experimental measurement can use a packed bed that preferably contains about $10 \times 10^{16}$ sites. From the estimated site concentration of $2.5 \times 10^{17}$ sites/gm catalyst, in order for the packed bed to contain $10 \times 10^{16}$ sites, it should have about 40 mg catalyst. Since 40 mg catalyst will give too short a packed bed, the amount of catalyst used is increased to about 70 mg to form a packed bed that has a length of 7 mm, since this will still be not so different from the indicated amount of sites desired. There is no need to use mixing with an inert powder. About 70 mg of the catalyst powder was precisely measured and used as the packed bed in the manner described above.

In this description, the embodiment 1 apparatus is used. The sample tube and furnace were placed between metal block 8 and sealing block 39. The vacuum pump was started to evacuate the vacuum chamber and the sample tube.

The catalyst was heated to the desired measurement temperature, which was 350° C. in this example. After 350° C. was reached and the gas background in the vacuum chamber had returned to their normal background, the device was ready for the measurement. A pulse of about $10^{14}$ molecules of a mixture of $O_2$—Ar (8:2 volume ratio) was injected and flows into the packed bed. The Ar and $O_2$ concentrations in the vacuum chamber due to elution from the sample tube versus time were recorded as the response curves for this pulse size. The sample tube was evacuated to remove adsorbed oxygen on the catalyst. In this example, the catalyst surface can be cleaned by evacuation; in other cases, esp. where there is dissociative adsorption, it may be necessary to use pulses or even a stream of a cleaning gas to clean the catalyst surface. In this example, desorption was slow and the catalyst was evacuated for 10 min to clean it; in some cases, it may be possible to perform the measurement at a temperature where desorption is fast, and the response curve also includes desorbed gas and the surface is cleaned as the response curve is measured.

Figure 5A:
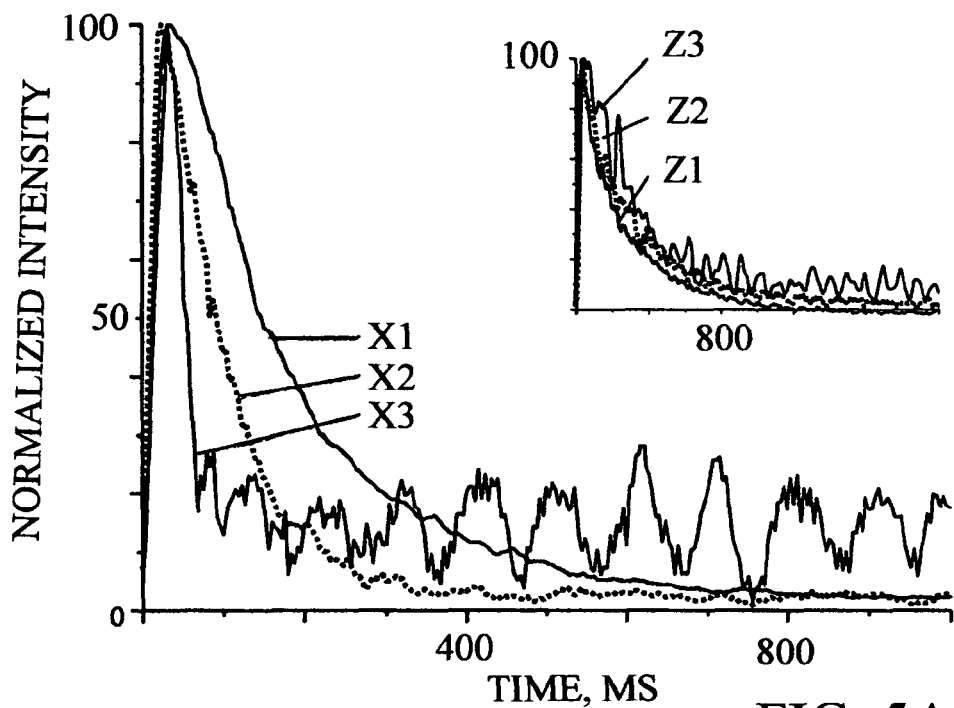
FIG. 5A and FIG. 5B are the experimental and simulation response curves, respectively, that measure the oxygen adsorption site concentration of a V—Mo-based catalyst powder.

When the catalyst surface has been cleaned, another pulse of the $O_2$—Ar mixture, but with a different number of molecules, was injected, and the Ar and $O_2$ response curves recorded. The steps of cleaning the surface, injecting a pulse of the $O_2$—Ar mixture, but each time comprising a different number of molecules, and measuring the Ar and $O_2$ response curves were repeated to get a series of response curves of pulses of different sizes. Three experimental $O_2$ response curves of different size pulses, $1.6 \times 10^{15}$, $5.3 \times 10^{14}$, and $3.3 \times 10^{13}$ $O_2$ molecules per pulse, are shown as curves X1, X2, and X3, respectively, in FIG. 5A. The inset in FIG. 5A shows the corresponding Ar response curves, Z1, Z2, and Z3, respectively. These curves are shown as normalized curves, that is, the intensities are shown as percentages of the maximum intensity. The data is that the $O_2$ response curves of different size pulses have different normalized shapes while the corresponding Ar response curves have the same normalized shapes (Z3 is the curve with the most noise, Z2 is the dotted curve, and Z1 is the most smooth curve).

Figure 5B:
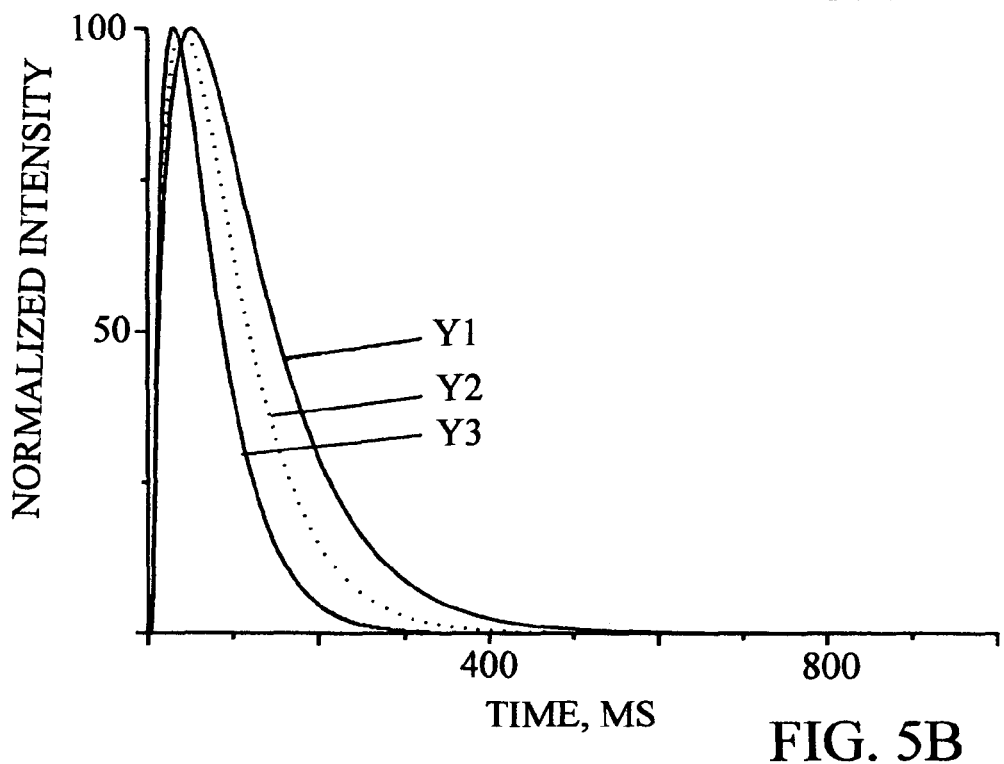

The set of reactor continuity equations (equations 2-4 described above) was solved using different values of their parameters to optimize the parameters for the best fit between the computed and experimental response curves. Curves Y1, Y2, and Y3 in FIG. 5B show the computed simulation curves, that correspond to curves X1, X2, and X3, respectively, after optimization of the parameters. The optimized parameters in this example were: $D_1=1.5 \times 10^{-8}$ m²/s, $D_2=3.5 \times 10^{-5}$ $d_r$ m²/s, $k'_{ad}=8.2 \times 10^{-15}$ (molec/mm packed bed)$^{-1}$ ms$^{-1}$, and $C_0=9.3 \times 10^{13}$ sites/mm packed bed. It can be calculated that $k_{ad}=k'_{ad} C_0=0.76$ ms$^{-1}$. The optimized active site concentration parameter in this example was $9.3 \times 10^{13}$ sites/mm packed bed, which can be used to easily compute the site concentration per gram of catalyst from that there was 0.8 mg catalyst in the 7 mm long packed bed. Hence, it was measured that the active site concentration per gram of catalyst is $8.1 \times 10^{17}$.

The above simulation used a kinetic expression for adsorption that was first order in site concentration. Similar calculations using a kinetic expression for adsorption that was second order in site concentration were also performed. In this example, the fit to the experimental data was better with a kinetic expression for adsorption that is first order in site concentration.

The number of sites present in the packed bed need to be limited, that is, sufficiently small, so that an individual pulse (within the range of pulse sizes that can be used) supply sufficient molecules to populate a significant fraction of the total sites. This was verified experimentally by checking that the reactant response curves from different size pulses have different normalized shapes. Simulations show that these fractions should be >1% of the total active sites. Also, the biggest pulse size that can be used is determined by the requirement to have Knudsen flow. That the gas pulse flowed by Knudsen flow was experimentally verified by checking that the normalized response curves of the internal standard inert gas (usually either argon or helium) do not change shape with pulses of different sizes. The upper limit on the pulse size is indicated by an inert gas response curve that just begins to get sharper, e.g. curve Z1 in the inset in FIG. 5A.

The number of active sites to be placed in the packed bed depends also on the rate of adsorption. It may need some experimentation to ensure that the packed bed contains a suitable amount. It is useful to use simulations with an estimated adsorption rate constant to estimate it. For this example, a simulation showed that for good sensitivity, there should be less than $1 \times 10^{16}$ sites in the packed bed if an embodiment 1 or 2 apparatus is used, and less than $2 \times 10^{17}$ sites in the packed bed if a suitable embodiment 3 apparatus is used.

Figure 6A:
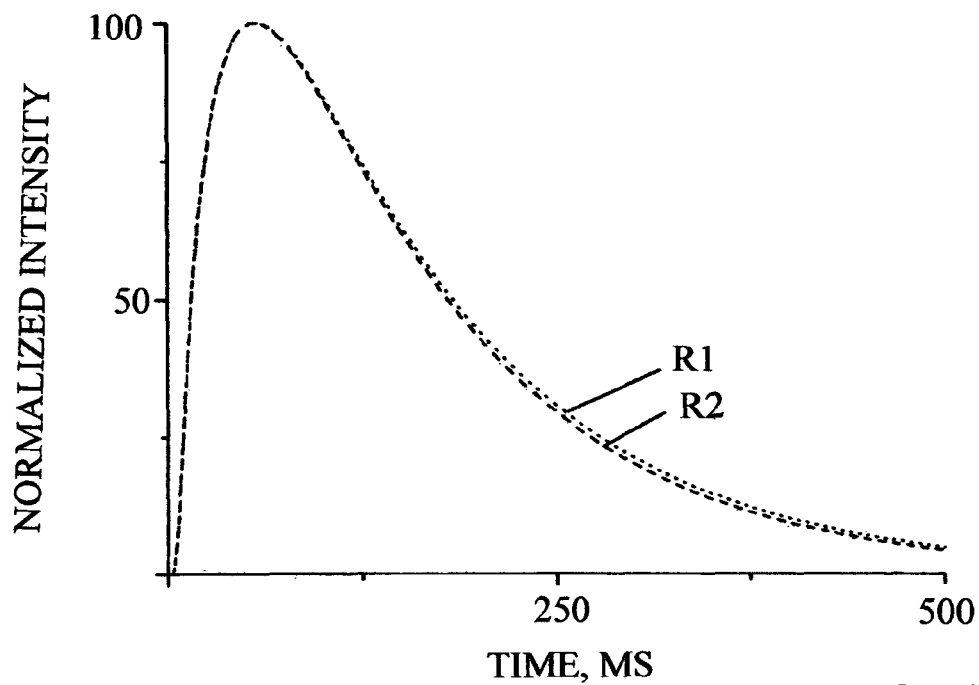
FIG. 6A is a simulation result of when adsorption is slow and shows that the response curves lack sensitive shape changes with pulse size.
Figure 6B:
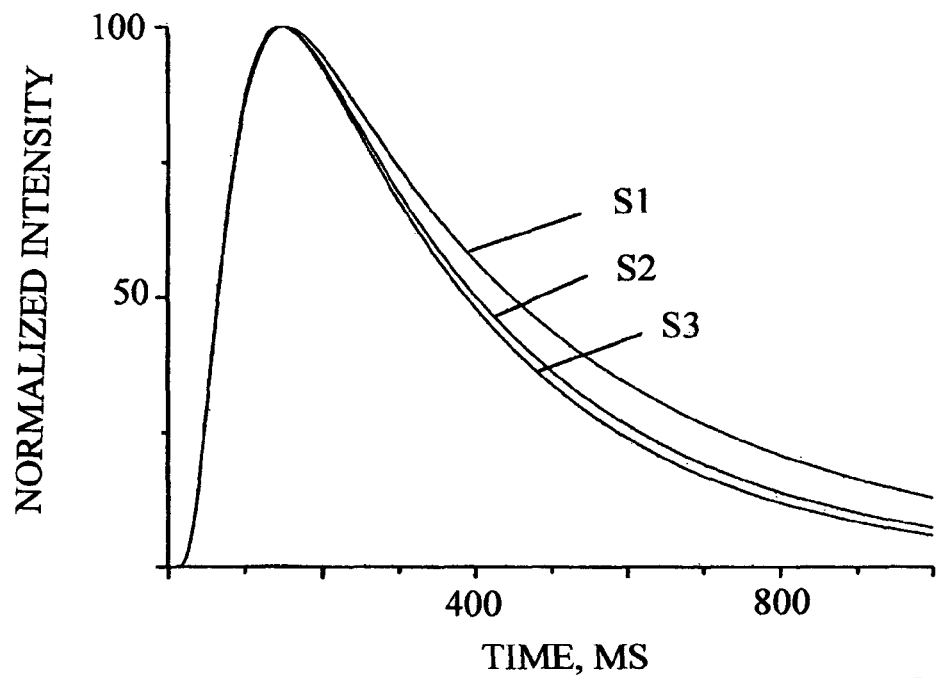
FIG. 6B is a simulation result that shows the response curves have enhanced curve shape changes due to adding a layer of smaller particles downstream of the catalyst packed bed.

For slow adsorption rates, the upper limit on the number of active sites in the packed bed can result in only a small fraction of the pulse getting adsorbed, even with small pulses. This makes the detection of shape changes difficult because the changes are only in a small part of the response curve, on the tail. Curves R1 and R2 in FIG. 6A shows a simulation of this situation, where their different size pulses are $2.0 \times 10^{15}$ and $1.0 \times 10^{14}$ molecules per pulse, respectively. The parameters in the simulation were: $D_1 = 1.5 \times 10^{-8}$ m$^2$/s, $D_2 = 3.5 \times 10^{-5} \times d_r$ m$^2$/s, $k'_{ad} = 1.0 \times 10^{-16}$ (molec/mm packed bed)$^{-1}$ ms$^{-1}$, $C_0 = 1.0 \times 10^{14}$ sites/mm packed bed, and a 10 mm long packed bed. It can be calculated that $k_{ad} = k'_{ad} C_0 = 0.01$ ms$^{-1}$ 10 s$^{-1}$. In this case, some means can be used to increase the residence time of the gas in the packed bed to increase the amount adsorbed. Possible means include using smaller particles, using a more diluted catalyst packed bed (to contain a smaller number of active sites per unit length) so that a longer packed bed can be used, or using a length of packed bed of inert small particles placed sequentially aft of the catalyst containing packed bed. Curves S1, S2, and S3 in FIG. 6B with different size pulses of $2.0 \times 10^{15}$, $5.0 \times 10^{14}$ and $1.0 \times 10^{13}$ molecules per pulse, respectively, were calculated from a simulation where a 10 mm long packed bed of inert small powder of effective diffusivity $1.0 \times 10^{-5}$ $d_r$ m$^2$/s was placed after the catalyst containing packed bed to facilitate the detection of shape changes. The shape changes have been made clearer. Using such simulations, the lower limit of the adsorption rate is estimated at about 1 s$^{-1}$. The upper limit is about 10000 s$^{-1}$, when the sticking probability is one.

Possible situations present during the measurement of the active site concentration include those where a reaction occurs after adsorption or two or more gases are coadsorbed to give a reaction. In these cases, it is possible to select to detect one or more molecular species for the response curves. E.g., when a mixture of oxygen and carbon monoxide is pulsed over a metal catalyst, they react to form carbon dioxide. The carbon dioxide response curves can be used in a similar way to the above to measure the active site concentration for carbon dioxide production. A particular molecular species may give normalized response curves that have more obvious shape changes, or it may be possible to select the input pulse composition to enhance the changes in a particular molecular species' normalized response curves.

It is useful to also perform a simulation using the optimized diffusivity parameters to ensure that the dimensions of the packed bed (bed length and particle size) give a sufficiently large diffusion time so that there is no intraparticle diffusion limitation. A simple simulation to check this is to simulate a response curve with an intraparticle effective diffusivity that is twice as large as the optimized parameter $D_1$ and confirm that there is no change in the shape of the normalized response curve. From such simulations, it is estimated that it is preferred that the catalyst powder particles are smaller than 0.050 mm in radius (or hydraulic radius).

What is claimed is:

1. A method for measuring the active site concentration of a catalyst powder, comprising the steps:
   (a) providing a metal block having a cavity with a plurality of valved openings on the cavity circumference;
   (b) providing valving means for a first valved opening and preparing a cleaning gas therein;
   (c) providing pulsed valving means for a second valved opening and preparing a feed gas comprising at least one reactant and an inert gas therein;
   (d) providing a demountable sample tube, disposing at least the catalyst powder as a packed bed therein, and attaching it at the upstream end to the mouth of the cavity, wherein the number of active sites on the catalyst powder is less than 100 times the number of adsorbate fragments in the largest gas pulse that is sufficiently small to satisfy the condition for Knudsen flow whereby the response curve shape of each gas pulse of a different size is different;
   (e) providing gas removing means that is in communication with the downstream end of the sample tube;
   (f) providing a furnace that encloses the packed bed;
   (g) heating and cleaning the catalyst powder by a delivery of cleaning gas using the valving means and removing gas using the gas removing means;
   (h) stopping the delivery of cleaning gas and desorbing adsorbed gas from the catalyst powder by heating and removing gas using the gas removal means to provide a vacuum in the sample tube;
   (i) providing for the packed bed to be at an adsorption temperature, using the pulsed valving means to deliver a feed gas pulse into the sample tube, and removing gas using the gas removal means, wherein the feed gas pulse is sufficiently small so that the feed gas flows in Knudsen flow;
   (j) providing at least two gas concentration measuring means that are in communication with the downstream end of the sample tube, measuring the response curves of the inert gas and at least one reactant as they are removed, and using the area of the inert gas response curve to calculate the injected pulse size;
   (k) using a mathematical model and fitting at least the response curve of the reactant to extract the active site concentration on the catalyst powder, and
   (l) repeating steps (g) to (k) using a different pulse size in step (i), wherein the largest and smallest pulses differ by at least ten-fold.

2. The method of claim 1 wherein the gas removing means in step (e) is a cylindrical vacuum chamber with a vacuum pump with pumping speed at least 1500 liters per second attached at the outlet end, and wherein the gas concentration measuring means are attached inside the vacuum chamber and the vacuum chamber is empty except for the gas concentration measuring means.

3. The method of claim 1 wherein the gas removing means in step (e) is alternatively an exhaust in step (g), a roughing pump in step (h), or a cylindrical vacuum chamber with a vacuum pump with pumping speed at least 1500 liters per second attached at the outlet end in step (i), and wherein the gas concentration measuring means are attached inside the vacuum chamber and the vacuum chamber is empty except for the gas concentration measuring means.

4. The method of claim 1 wherein the cavity in step (a) is at least 0.1 ml in volume and in immediate communication with the sample tube.

5. The method of claim 1 further including disposing an auxiliary packed bed of inert particles comprising a particle size between 1 and 200 micron downstream of the packed bed in step (d).

6. The method of claim 1 wherein the packed bed in step (d) is of sufficient length so that the bed diffusion time constant is larger than the intraparticle diffusion time constant in the catalyst powder, and wherein the packed bed may include a diffusively similar inert powder to get it to the required length.

7. The method of claim 1 further including measuring the response curves of at least one product gas in step (j) and fitting the response curve of the product gas in step (k).

* * * * *